(12) United States Patent
Yoshina et al.

(10) Patent No.: US 9,457,924 B2
(45) Date of Patent: Oct. 4, 2016

(54) PHARMACEUTICAL PACKAGING APPARATUS, METHOD OF DETERMINING REMAINING QUANTITY OF PHARMACEUTICAL PACKAGING PAPER AND PHARMACEUTICAL PACKAGING PAPER ROLL

(71) Applicant: YUYAMA MFG. CO., LTD., Toyonaka-shi, Osaka (JP)

(72) Inventors: Katsunori Yoshina, Toyonaka (JP); Tomohiro Sugimoto, Toyonaka (JP); Noriyoshi Fujii, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 0 days.

(21) Appl. No.: 14/780,453

(22) PCT Filed: Mar. 18, 2014

(86) PCT No.: PCT/JP2014/057405
§ 371 (c)(1),
(2) Date: Sep. 25, 2015

(87) PCT Pub. No.: WO2014/156850
PCT Pub. Date: Oct. 2, 2014

(65) Prior Publication Data
US 2016/0059983 A1    Mar. 3, 2016

(30) Foreign Application Priority Data

Mar. 25, 2013 (JP) ................................. 2013-061923
May 17, 2013 (JP) ................................. 2013-105104

(51) Int. Cl.
*B65B 57/04* (2006.01)
*G01N 33/34* (2006.01)
(Continued)

(52) U.S. Cl.
CPC ............... *B65B 57/04* (2013.01); *B65H 18/28* (2013.01); *B65H 26/06* (2013.01); *B65H 43/00* (2013.01);
(Continued)

(58) Field of Classification Search
CPC ....... B65B 57/04; B65B 57/02; B65H 43/00; B65H 18/28; B65H 26/06; B65H 2553/52; B65H 2511/114; B65H 2220/03; G01N 33/346

See application file for complete search history.

(56) References Cited

U.S. PATENT DOCUMENTS 3,652,357 A * 3/1972 Vogel ..................... B65B 57/04
156/203
3,688,465 A * 9/1972 Benitez ................... B65B 57/04
53/120

(Continued)

FOREIGN PATENT DOCUMENTS

JP        2909450 B       6/1999
JP      2001-055202 A     2/2001

(Continued)

OTHER PUBLICATIONS

WIPO ISA/JP, International Search Report with English translation, issued in International Application No. PCT/JP2014/057405, mailing date Jul. 1, 2014, 10 pages.

(Continued)

*Primary Examiner* — Ramesh Patel
(74) *Attorney, Agent, or Firm* — Masuvalley & Partners

(57) ABSTRACT

Medicine packaging apparatuses and methods for accurately determining a remaining sheet amount of a medicine packaging sheet are described. The apparatus includes: a roll support section to which a core tube of a medicine packaging sheet roll is attached; a sensor disposed in the roll support section for outputting a count value according to a rotation amount; a wireless reader-writer unit for writing information to a core tube IC tag and reading said information; an information generation section for generating information to be written to the core tube IC tag; a remaining sheet amount estimation section for estimating a current amount of remaining sheet based on the information and dimensional information of the core tube; and a controller which selectively performs an operation if a reference time-point count value is not yet written to the core tube IC tag and another operation if the count value is already written thereto.

20 Claims, 12 Drawing Sheets

(51) Int. Cl.
*B65H 43/00* (2006.01)
*B65H 18/28* (2006.01)
*B65H 26/06* (2006.01)
*B65B 57/02* (2006.01)

(52) U.S. Cl.
CPC ............. *G01N 33/346* (2013.01); *B65B 57/02* (2013.01); *B65H 2511/114* (2013.01); *B65H 2553/52* (2013.01)

(56) References Cited

U.S. PATENT DOCUMENTS

| | | | |
|---|---|---|---|
| 4,467,589 A * | 8/1984 | van Maanen | B65B 41/18 156/164 |
| 4,831,461 A * | 5/1989 | Ohta | H04N 1/121 250/589 |
| 4,987,728 A * | 1/1991 | Ventura | B65B 9/04 53/389.5 |
| 5,667,617 A * | 9/1997 | Fogle | B65H 18/28 156/184 |
| 5,967,445 A | 10/1999 | Yuyama et al. | |
| 6,059,222 A | 5/2000 | Yuyama et al. | |
| 6,286,780 B1 | 9/2001 | Yuyama et al. | |
| 6,301,862 B1 | 10/2001 | Yuyama et al. | |
| 7,596,925 B2 | 10/2009 | Yuyama et al. | |
| 7,827,764 B2 | 11/2010 | Yuyama et al. | |
| 2002/0053184 A1* | 5/2002 | Hook | B65B 9/093 53/396 |
| 2007/0286617 A1* | 12/2007 | Tanaka | G03G 15/0863 399/30 |
| 2008/0029530 A1 | 2/2008 | Yuyama et al. | |
| 2008/0030796 A1* | 2/2008 | Sakamoto | G06K 1/18 358/444 |
| 2008/0315512 A1* | 12/2008 | Naruoka | B65H 5/023 271/265.01 |
| 2009/0085451 A1 | 4/2009 | Yuyama et al. | |
| 2010/0077699 A1* | 4/2010 | Hatsuno | B29C 66/431 53/154 |
| 2010/0107555 A1* | 5/2010 | Yuyama | B65B 9/08 53/131.2 |
| 2012/0047849 A1* | 3/2012 | Koenigkramer | B65B 9/2028 53/416 |
| 2013/0016902 A1* | 1/2013 | Suino | G06K 15/189 382/164 |

FOREIGN PATENT DOCUMENTS

| | | |
|---|---|---|
| JP | 2002-011074 A | 1/2002 |
| JP | 2002-017815 A | 1/2002 |
| JP | 2003-341938 A | 12/2003 |
| JP | 2004-224444 A | 8/2004 |
| JP | 2005-230242 A | 9/2005 |
| JP | 2007-126215 A | 5/2007 |
| JP | 2009-227469 A | 10/2009 |
| JP | 2010-035675 A | 2/2010 |
| JP | 2010-149933 A | 7/2010 |
| JP | 4564437 B | 10/2010 |
| JP | 2011-148542 A | 8/2011 |
| JP | 2012-082020 A | 4/2012 |
| JP | 2012-214255 A | 11/2012 |
| WO | 2013/133130 A | 9/2013 |

OTHER PUBLICATIONS

IB of WIPO Authorized Officer Yukari Nakamura, International Preliminary Report on Patentability, issued in International Application No. PCT/JP2014/057405, mailing date Oct. 1, 2015, 7 pages.

* cited by examiner

Reference Time-Point

Sheet Used Amount
= P packages

Sheet Used Amount
= P+1 packages

Sheet In-Use Time-Point

Sheet Used Amount
= Q packages

Current Time-Point

Sheet Used Amount
= Q+1 packages

PHARMACEUTICAL PACKAGING APPARATUS, METHOD OF DETERMINING REMAINING QUANTITY OF PHARMACEUTICAL PACKAGING PAPER AND PHARMACEUTICAL PACKAGING PAPER ROLL

This application is a national phase application under 35 U.S.C. §371 of International Application Serial No. PCT/JP2014/057405, filed on Mar. 18, 2014, and claims the priority under 35 U.S.C. §119 to Japan Patent Application No. 2013-061923, filed on Mar. 25, 2013, and Japan Patent Application No. 2013-105104, filed May 17, 2013 which are hereby expressly incorporated by reference in their entirety for all purposes.

TECHNICAL FIELD

The present invention relates to medicine packaging apparatuses which package medicine by one package using packaging sheet; medicine packaging sheet remaining amount determination methods; and medicine packaging sheet rolls.

BACKGROUND OF THE INVENTION

Patent Literature 1: JP-B 4564437 discloses a medicine dispensing apparatus serving as a medicine packaging apparatus which packages medicine such as tablets and powders by one package using a medicine packaging sheet while printing patient's name, time and date for taking medicines, etc. on the medicine packaging sheet.

The medicine dispensing apparatus of the Patent Literature 1 uses a medicine packaging sheet roll as a supply source of a medicine packaging sheet for packaging the medicine. The medicine packaging sheet is overlapped with an ink ribbon at a location of a printing head, so that the printing head prints the patient's name, time and date of taking the medicines, etc. The printed medicine packaging sheet is then folded into two so that the folded sheet has its open end facing upward to catch one package amount of the medicine such as tablets and powders.

If the apparatus is capable of indicating an amount of medicine packaging sheet remaining in the medicine packaging sheet roll (a remaining amount of a rolled material), the user should be able to know how many more packages he/she will be able to make by using the remaining medicine packaging sheet, and therefore they can plan for a best way which will minimize wasted amount in the medicine packaging sheet.

The remaining amount of the medicine packaging sheet can be obtained by subtracting the length which has been used from the original length of the medicine packaging sheet roll. A problem here is that there are always personal differences among human operators in the amount when cutting the medicine packaging sheet roll at an end of the roll at the time of manufacture; in other words, the original length of the roll is not always the same. Also, there is always some differences between production lots. For these reasons, it is impossible to determine a precise remainder although it is possible to get an approximate length of the remainder. This is because the rolls are always made to have some extra length over a specified length to compensate for non-exact nature of the roll cutting operation.

A remaining amount of the medicine packaging sheet can also be obtained by another method: as the medicine packaging sheet is unwound, an amount of rotation of the medicine packaging sheet roll is monitored to determine the diameter of the medicine packaging sheet roll, and from this diameter and a thickness of the medicine packaging sheet, it is possible to calculate the remaining amount. A problem here, however, is that the thickness of the medicine packaging sheet which is required in this method is not a thickness of the sheet itself, but a thickness which includes layers of air between layers of medicine packaging sheet laminated in the form of a roll.

However, the layers of air can vary depending on many different factors such as a tension of sheet when manufacturing the medicine packaging sheet roll, so it is impossible to know an exact thickness with accurate thickness of the layers of air. For these reasons, it has been difficult to let the user know an exact number of packages he/she can make from the remaining amount of sheet.

In view of the above aforementioned situations, embodiments of the present invention provides a medicine packaging apparatus, a medicine packaging sheet remaining amount determination method, and a medicine packaging sheet roll, for accurately determining a remaining amount of medicine packaging sheet.

SUMMARY OF THE INVENTION

In order to solve the above-described problems, the present invention provides a medicine packaging apparatus which includes: a roll support section having a rotating shaft portion to which a core tube of a medicine packaging sheet roll is attached; a rotation amount information outputting section for an output of rotation amount information which indicates a rotation amount of the rotating shaft portion; an information writing/reading section for writing information to and reading the written information from a storage medium provided inside the core tube attached to the roll support section; an information generation section for generating, as information are written to the storage medium, rotation amount information as of reference sheet-remaining amount timing which is the rotation amount information upon unwinding of a packaging sheet by a predetermined length from the medicine packaging sheet roll at a reference time-point; one or a plural pieces of rotation amount information as of individual current sheet-remaining amount obtaining timings each of which is the rotation amount information upon unwinding of the packaging sheet by the predetermined length from the medicine packaging sheet roll at a packaging sheet in-use time-point after the reference time-point; and an amount of sheet used from the reference time-point through the packaging sheet in-use time-point; and a remaining sheet amount estimation section for estimating a current amount of remaining sheet based on the rotation amount information as of reference sheet-remaining amount timing, the rotation amount information as of individual current sheet-remaining amount obtaining timing, the amount of sheet used from the reference time-point through the packaging sheet in-use time-point, and dimensional information of the core tube.

According to the arrangement described above, a current amount of remaining sheet is estimated based on the rotation amount information as of reference sheet-remaining amount timing, the rotation amount information as of individual current sheet-remaining amount obtaining timing, the amount of sheet used from the reference time-point through the packaging sheet in-use time-point, and dimensional information of the core tube. Therefore, there is no need for using the thickness of the medicine packaging sheet or the layers of air in calculation of the remaining amount, and thus, it is possible to show the user an accurate amount of the remaining sheet.

Also, the medicine packaging apparatus according to the present invention includes: a roll support section including a rotating shaft portion to which a core tube of a medicine packaging sheet roll is attached; a rotation amount information outputting section for an output of rotation amount of the rotating shaft portion; an information generation section for generating: a first rotation amount upon unwinding of a predetermined length of a packaging sheet from the medicine packaging sheet roll which has a first remaining amount of the packaging sheet; a second rotation amount upon unwinding of the predetermined length of the packaging sheet from the medicine packaging sheet roll which has a second remaining amount of the packaging sheet, the second remaining amount being a smaller amount than the first amount; and an amount of used sheet which is a difference between the first amount and the second amount; a communications section which writes/reads information generated by the information generation section to/from a storage medium provided in the core tube; and a remaining sheet amount calculation section for calculating an amount of remaining sheet after the packaging sheet is unwound by the predetermined length from the medicine packaging sheet roll which has the second remaining amount of the packaging sheet, based on information read by the communications section and dimensional information of the core tube.

According to the arrangement described above, calculation of an amount of remaining sheet after the packaging sheet is unwound by the predetermined length from the medicine packaging sheet roll which has the second remaining amount of the packaging sheet is based on the first rotation amount, the second rotation amount, the amount of used sheet and the dimensional information of the core tube. Therefore, there is no need for using the thickness of the medicine packaging sheet or the layers of air in calculation of the remaining amount, and it is possible to show the user an accurate amount of the remaining sheet.

The apparatus may further include a controller which performs an operation if the rotation amount information as of reference sheet-remaining amount timing or the above-defined first rotation amount is not yet written to the storage medium, and performs another operation if the information or the first rotation amount is already written thereto.

In one embodiment, if the rotation amount information, as of reference sheet-remaining amount timing or the above-defined first rotation amount, is not yet written to the storage medium, the controller performs a process of obtaining rotation amount information each time the packaging sheet is unwound from the medicine packaging sheet roll by the predetermined length until a latest rotation amount information is within a predetermined range with respect to a previous rotation amount information for a predetermined number of times, whereupon the controller moves to a process of obtaining the rotation amount information as of reference sheet-remaining amount timing or the above-mentioned first rotation amount.

As the process of obtaining the rotation amount information, as of reference sheet-remaining amount timing or the above-defined first rotation amount, the controller may perform a process of: obtaining rotation amount information for a plurality of times each time the packaging sheet is unwound from the medicine packaging sheet roll by the predetermined length; calculating an average value or a mode value of them and setting the calculated value as rotation amount information as of a predetermined unwinding timing; and then performs a process using this rotation amount information as the rotation amount information as of reference sheet-remaining amount timing or the above-defined first rotation amount.

In another embodiment, if the rotation amount information as of reference sheet-remaining amount timing or the above-defined first rotation amount is already written to the storage medium but said one or plural pieces of rotation amount information as of individual current sheet-remaining amount obtaining timings or the above-defined second rotation amount, which are to be used in estimation of the remaining sheet amount, are not, then the controller performs a process of obtaining rotation amount information as of individual current sheet-remaining amount obtaining timing or the above-defined second rotation amount and writing it to the storage medium at a time when the packaging sheet is unwound from the medicine packaging sheet roll by the predetermined length, for a single or a plurality of times, whereas if the rotation amount information as of reference sheet-remaining amount timing or the above-defined first rotation amount is already written to the storage medium and said one or plural pieces of rotation amount information as of individual current sheet-remaining amount obtaining timing or the above-defined second rotation amount for use in the estimation are also written, then the controller performs a data updating process of obtaining rotation amount information as of individual current sheet-remaining amount obtaining timing or the above-defined second rotation amount each time the packaging sheet is unwound from the medicine packaging sheet roll by the predetermined length, and using the obtained information to overwrite one or an oldest piece of rotation amount information as of individual current sheet-remaining amount obtaining timing or the above-defined second rotation amount in the storage medium.

Information sending/receiving between the storage medium and the information reading section may be made via antennas disposed in the roll support section. The antennas may have their faces disposed in planes extending across an axis of the rotating shaft portion.

Further, the medicine packaging apparatus according yet to another embodiment of the present invention is a medicine packaging apparatus for packaging medicine by one package by using a medicine packaging sheet roll, and includes: a rotation amount information outputting section for an output of rotation amount information indicating a rotation amount of a rotating shaft portion to which a core tube of the medicine packaging sheet roll is attached; a used-amount information outputting section for an output of used-amount information indicating an unwound amount of the packaging sheet of the medicine packaging sheet roll; an information reading section for reading rotation amount information as of reference sheet-remaining amount timing, which is rotation amount information indicating a rotation amount of the core tube of the medicine packaging sheet roll upon unwinding of the medicine packaging sheet roll by a predetermined length at a reference time-point, from a storage medium provided in the core tube of the medicine packaging sheet roll; an information generation section for generation of: rotation amount information as of individual current sheet-remaining amount obtaining timing which includes one or a plural pieces of rotation amount information each indicating a rotation amount of the core tube of the medicine packaging sheet roll upon unwinding of the medicine packaging sheet roll by the predetermined length at packaging sheet in-use time-point after the reference time-point; and an amount of used sheet from the reference time-point through the packaging sheet in-use time-point; and a remaining sheet amount estimation section for estimating a current amount of remaining sheet based on the rotation amount information as of reference sheet-remaining amount timing, the rotation amount information as of individual current sheet-remaining amount obtaining timing, the amount of sheet use from the reference time-point through the packaging sheet in-use time-point, and dimensional information of the core tube.

In this embodiment, a current amount of remaining sheet is estimated based on the rotation amount information as of reference sheet-remaining amount timing, the rotation amount information as of individual current sheet-remaining amount obtaining timing, the amount of sheet use from the reference time-point through the packaging sheet in-use time-point, and dimensional information of the core tube. Therefore, there is no need for using the thickness of the medicine packaging sheet or the layers of air in calculation of the remaining amount, and it is possible to show the user an accurate amount of the remaining sheet.

The apparatus may make comparison between an amount of sheet required to finish a medicine packaging task and the remaining sheet amount, and issue a warning if a comparison result is out of an acceptable range.

The medicine packaging sheet roll according to the embodiments of the present invention is a medicine packaging sheet roll for use in the above-described medicine packaging apparatuses, and has a storage medium in the core tube. The storage medium may store dimensional information of the core tube.

In the medicine packaging sheet roll, the core tube may include an inner tube portion and an outer tube portion, and the storage medium may be disposed in a gap between the inner tube portion and the outer tube portion.

A medicine packaging sheet remaining amount determination method according to the present invention is a medicine packaging sheet remaining amount determination method of a medicine packaging apparatus for packaging medicine by one package by using a medicine packaging sheet roll. The method includes: a step of obtaining from a storage medium provided in a core tube of the medicine packaging sheet roll, rotation amount information as of reference sheet-remaining amount timing, which is rotation amount information indicating a rotation amount of the core tube of the medicine packaging sheet roll upon unwinding of the medicine packaging sheet roll by a predetermined length at a reference time-point; rotation amount information as of individual current sheet-remaining amount obtaining timing which includes one or a plural pieces of rotation amount information each indicating a rotation amount of the core tube of the medicine packaging sheet roll upon unwinding of the medicine packaging sheet roll by the predetermined length at a packaging sheet in-use time-point after the reference time-point; and an amount of sheet use from the reference time-point through the packaging sheet in-use time-point; and a step of estimating a current amount of remaining sheet based on the rotation amount information as of reference sheet-remaining amount timing, the rotation amount information as of individual current sheet-remaining amount obtaining timing, the amount of used sheet from the reference time-point through the packaging sheet in-use time-point, and dimensional information of the core tube.

According to this embodiment, a current amount of remaining sheet is estimated based on the rotation amount information as of reference sheet-remaining amount timing, the rotation amount information as of individual current sheet-remaining amount obtaining timing, the amount of used sheet from the reference time-point through the packaging sheet in-use time-point, and dimensional information of the core tube. Therefore, there is no need for using the thickness of the medicine packaging sheet or the layers of air in calculation of the remaining amount, and thus, it is possible to show the user an accurate amount of the remaining sheet.

Also, a medicine packaging sheet remaining amount determination method according to the present invention is a medicine packaging sheet remaining amount determination method of a medicine packaging apparatus for packaging medicine by one package by using a medicine packaging sheet roll. The method includes: a step of obtaining, from a storage medium provided in a core tube of the medicine packaging sheet roll, a first rotation amount which is a rotation amount of the core tube of the medicine packaging sheet roll upon unwinding of a predetermined length of a packaging sheet from the medicine packaging sheet roll which has a first remaining amount of the packaging sheet, a second rotation amount which is the rotation amount of the core tube upon unwinding of the predetermined length of the packaging sheet from the medicine packaging sheet roll which has a second remaining amount of the packaging sheet as a smaller amount than the first amount, and an amount of used sheet which is a difference between the first amount and the second amount; and a step of calculating a remaining sheet amount which is an amount after the packaging sheet is unwound by the predetermined length from the medicine packaging sheet roll which has the second remaining amount of the packaging sheet, based on the first rotation amount, the second rotation amount, the amount of sheet use and dimensional information of the core tube.

According to the arrangement described above, calculation of an amount of remaining sheet after the packaging sheet is unwound by the predetermined length from the medicine packaging sheet roll which has the second remaining amount of the packaging sheet is based on the first rotation amount, the second rotation amount, the amount of sheet use and dimensional information of the core tube. Therefore, there is no need for using the thickness of the medicine packaging sheet or the layers of air in calculation of the remaining amount, and thus, it is possible to show the user an accurate amount of the remaining sheet.

Also, a medicine packaging apparatus according to the present invention is for packaging medicine and making a print using an ink ribbon roll and a medicine packaging sheet roll. The apparatus includes: a gap making section for making a first state in which a printing head and a backup section opposed thereto are spaced from each other, and a second state in which they are further spaced than in the first state; a winding controller for controlling a winding of an ink ribbon to remove a slack in the ink ribbon in the ink ribbon roll in the second state; and a controller for making the second state and performing a control of the winding of the ink ribbon upon determination that there is a possibility for the medicine packaging sheet roll to be replaced.

The apparatus may include a printing and packaging unit including a printing section which makes use of the ink ribbon roll and the medicine packaging sheet roll, and a packaging section which performs a medicine packaging operation. In this embodiment, the printing and packaging unit is movable out of a main body of the apparatus toward a front side, and the controller makes the second state and performs the control of the winding of the ink ribbon upon detection that the printing and packaging unit is moved from within main body of the apparatus toward the front side and determination that there is a possibility for the medicine packaging sheet roll to be replaced.

In another embodiment, the controller may determine that there is a possibility for the medicine packaging sheet roll to be replaced if it becomes unable to read information from a storage medium through an information reading section which reads information from the storage medium that is disposed in a core tube of the medicine packaging sheet roll.

The apparatus may further include a detection section for detecting whether or not the core tube is removed from a rotating shaft portion serving as a rotation shaft for the core tube. In this embodiment, the controller determines the possibility of replacing the medicine packaging sheet roll upon detection via the detection section that the core tube is removed from the rotating shaft portion.

The apparatus may further include a detection section for detecting an end of the medicine packaging sheet roll. In the present embodiment, the controller determines the possibility of replacing the medicine packaging sheet roll upon detection of the end of the medicine packaging sheet roll via the detection section.

Also, a medicine packaging apparatus according to the embodiment of the present invention is a medicine packaging apparatus for packaging medicine and making a print using an ink ribbon roll and a medicine packaging sheet roll. The apparatus includes: a gap making section for making a first state in which a printing head and a backup section opposed thereto are spaced from each other by a first distance, and a second state in which they are spaced from each other by a second distance which is longer than the first distance; a winding controller for controlling a winding of an ink ribbon to remove a slack in the ink ribbon in the ink ribbon roll in the second state; and a controller for making the second state and performing a control of the winding of the ink ribbon upon determination that there is a possibility for the ink ribbon roll to be replaced.

There may be an arrangement that the printing and packaging unit includes a printing section which makes use of the ink ribbon roll and the medicine packaging sheet roll, and a packaging section which makes a medicine packaging operation, and the printing and packaging unit is movable out of a main body of the apparatus toward a front side. In this embodiment, the controller makes the second state and performs the control of the winding of the ink ribbon upon detecting that the printing and packaging unit is moved from inside of the apparatus main body toward the front side and determines that there is a possibility for the medicine packaging sheet roll to be replaced.

The apparatus may further include a detection section for detecting an end of the ink ribbon roll. In this embodiment, the controller determines that there is a possibility for the ink ribbon roll to be replaced upon detection of the end of the ribbon roll via the detection section.

There may also be an arrangement that a supply core of the ink ribbon roll receives a braking operation in the second state when the control of the winding is performed to the ink ribbon whereas the braking operation is ceased when changing from the second state to the first state.

The present invention provides accurate determination of the remaining amount of sheet in the medicine packaging apparatus. Therefore, the user is advantageously informed with a quantity of packages he/she will be able to make using the remaining medicine packaging sheet, and can plan for a best way to minimize wasted amount in the medicine packaging sheet.

BRIEF DESCRIPTION OF DRAWINGS

The present disclosure is described in conjunction with the appended figures.

DETAILED DESCRIPTION OF THE INVENTION

Figure 1:
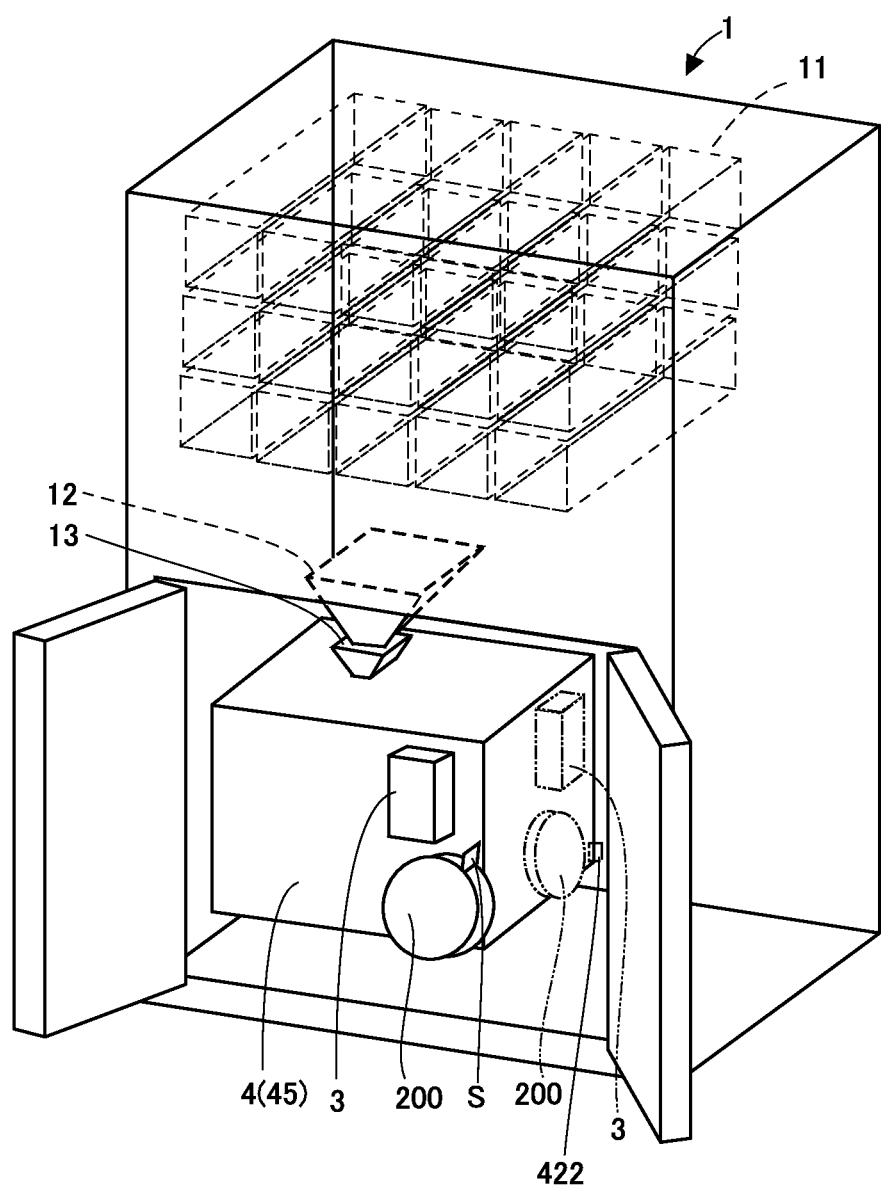
FIG. 1 is a perspective view which shows a schematic structure of a medicine packaging apparatus according to one embodiment of the present invention.

Hereinafter, embodiments of the present invention will be described with reference to the attached drawings. As shown in FIG. 1, a medicine packaging apparatus 1 according to a present embodiment has a main body, which includes: a medicine housing dispensing unit 11 for housing medicine and dispensing of the medicine by one package in accordance with prescription; hoppers 12, 13 for receiving the medicine dispensed by one package; and a printing and packaging unit 4 to which a medicine packaging sheet roll 200 and an ink ribbon cassette 3 are detachably attached for making print on a medicine packaging sheet S supplied from the medicine packaging sheet roll 200 and packaging by one package the medicine supplied from the hoppers 12, 13 by using this medicine packaging sheet S. In order for easy replacement of the ink ribbon cassette 3 and the medicine packaging sheet roll 200, the printing and packaging unit 4 is made movable, outward from the apparatus main body, by means of rails, hinges, etc. When the printing and packaging unit 4 is moved from inside the apparatus main body toward outside the movement can be detected by a detection switch 422 for example.

Figure 2:
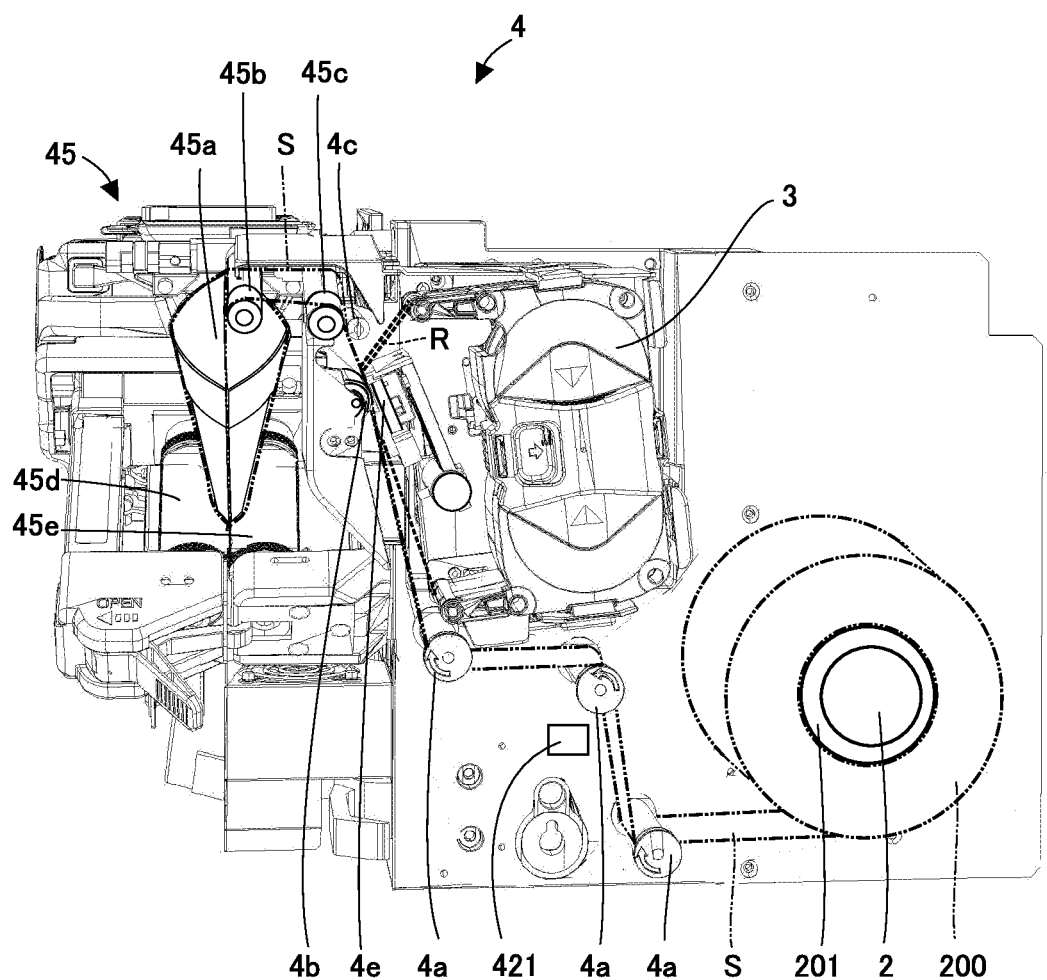
FIG. 2 is a perspective view which shows a printing and packaging unit included in the medicine packaging apparatus shown in FIG. 1.
Figure 3:
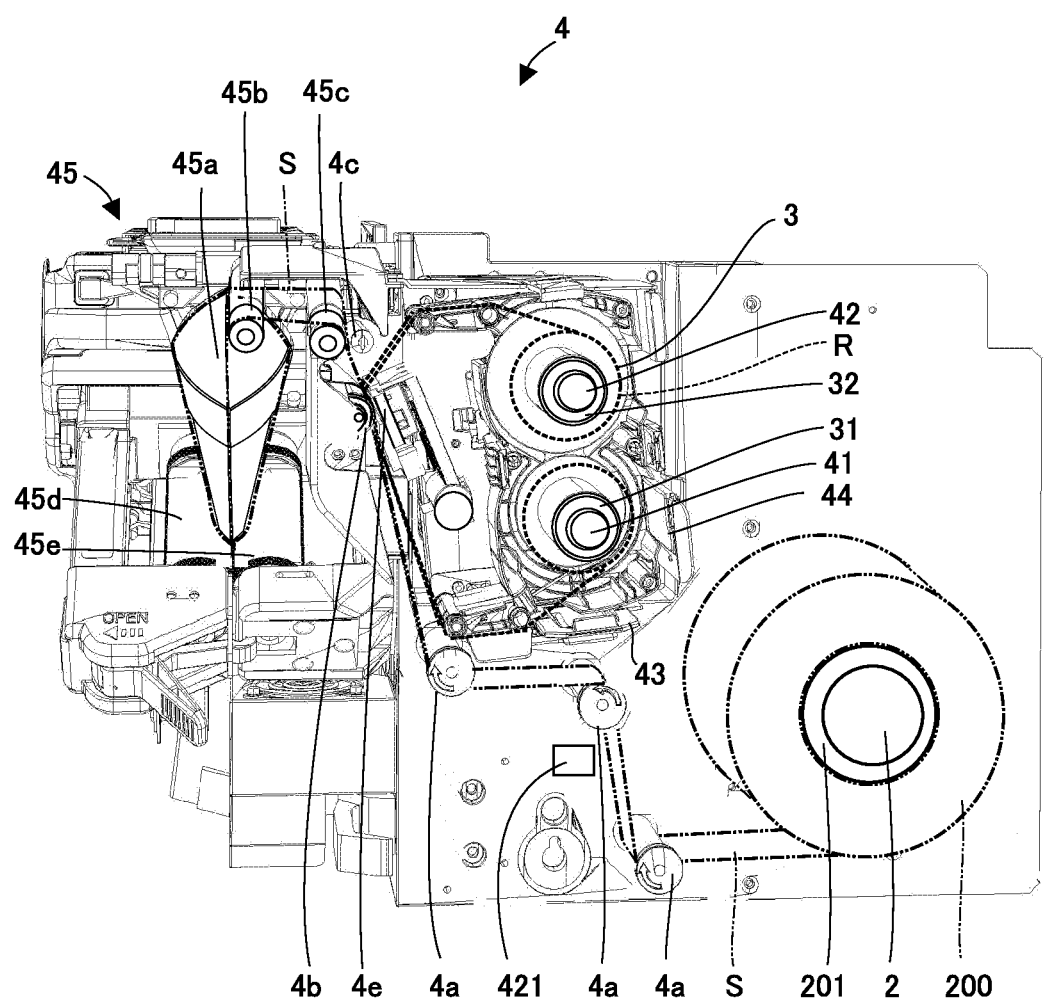
FIG. 3 is a perspective view of the printing and packaging unit shown in FIG. 2, with a cover of an ink ribbon cassette and other components are removed therefrom.

FIG. 2 and FIG. 3 are perspective views illustrating the printing and packaging unit 4 with the medicine packaging sheet roll 200 and the ink ribbon cassette 3 attached thereto. FIG. 2 and FIG. 3 also show a packaging section 45 of the printing and packaging unit 4. The packaging section 45 is an operation unit which introduces medicine from an opening of the medicine packaging sheet S, and then thermally seals the medicine packaging sheet S thereby sealing the medicine. The medicine packaging sheet S hooks onto three guide shafts 4a', passes through between a back-up roller 4b and a printing head 4e, and is passed through to hook onto a guide shaft 4c. The ink ribbon cassette 3 incorporates therein an ink ribbon R, which is guided by a tape guide of the printing and packaging unit 4, passed through between the back-up roller 4b and the printing head 4e, then moved away from the medicine packaging sheet S after printing, and returned to the ink ribbon cassette 3.

Figure 4:
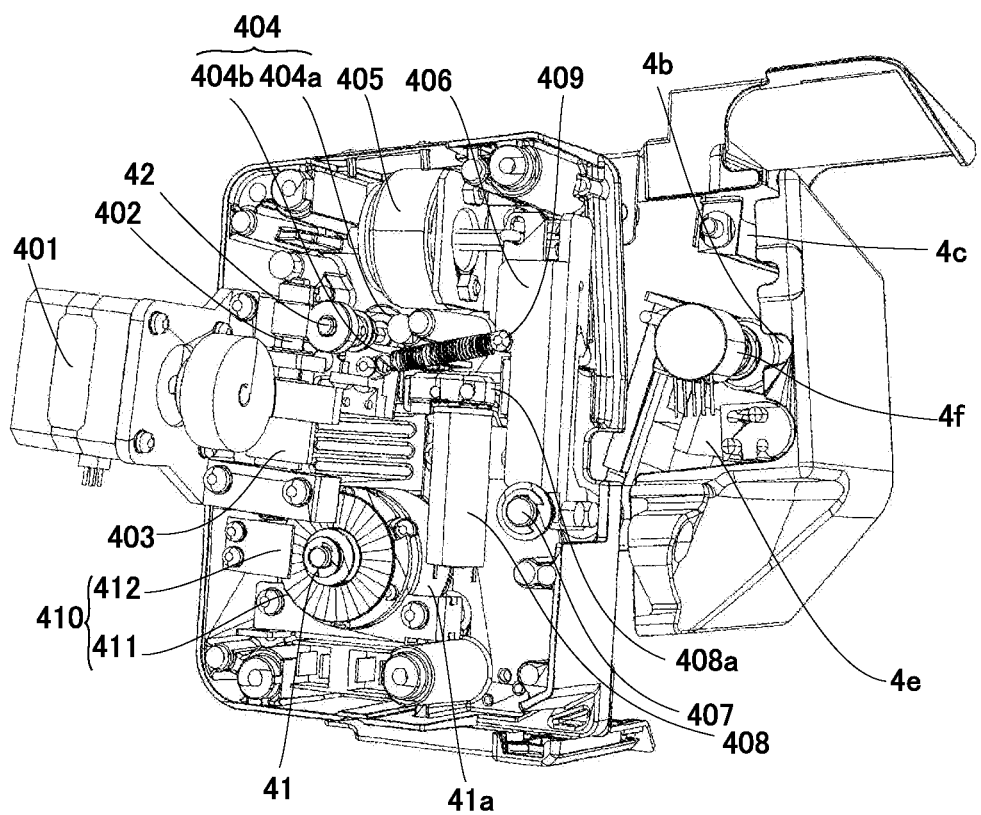
FIG. 4 is a perspective view which shows a back side of a printing section inside the printing and packaging unit shown in FIG. 2.

FIG. 4 is a perspective view of the printing and packaging unit 4 seen from a back side. As shown in this figure, a unit in which the printing head 4e is mounted is swingably supported around a shaft 407. Specifically, a link member 406 and the printing head 4e are attached to the shaft 407, and as a head solenoid 405 is turned ON, the link member 406 is actuated to pivot the printing head 4e around the shaft 407. The printing head 4e moves toward the back-up roller 4b and presses the ink ribbon R onto the medicine packaging sheet S so that printing operation can be started.

Also as shown in FIG. 2 and FIG. 3, rotatable curved guide rollers 45b, 45c are disposed to turn the transporting direction of the medicine packaging sheet S just before an unfolding guide 45a of the packaging section 45, at a position near the guide shaft 4c (on the downstream side in terms of the transporting direction of the medicine packaging sheet S) which guides the medicine packaging sheet S. On a back side of the unfolding guide 45a, there is provided a hopper for introducing the medicine to the medicine packaging sheet S. The unfolding guide 45a unfolds the two-folded medicine packaging sheet S, thereby forming an opening for the hopper to insert its medicine outlet (nozzle). The packaging section 45 has a pair of heater rollers 45d, 45e below the unfolding guide 45a. An unillustrated traveling roller is provided below the heater rollers 45d, 45e. The heater rollers 45d, 45e are driven to rotate by an unillustrated drive mechanism constituted by motors, linear gears, intermittent gears, and others. The heater rollers 45d, 45e can move the medicine packaging sheet S at a traveling speed $V_2$ which will be described later.

The printing and packaging unit 4 includes a supply-side support shaft 41, which supports a supply core 31 of the ink ribbon cassette 3, and is rotated as the supply core 31 rotates. A winding-side support shaft 42 supports a winding core 32 of the ink ribbon cassette 3, and rotationally drives the winding core 32. The ink ribbon cassette 3 is attached to a storage section, on an outside of which two platy antennas 43, 44 are provided. The two antennas 43, 44 have their radio wave transmission/reception surfaces opposed to a circumferential surface of the supply-side support shaft 41 (opposed to a circumferential surface of the supply core 31 when the ink ribbon cassette 3 is installed), with the radio wave transmission/reception surfaces facing in mutually crossing directions (desirably being disposed at a 90° angle).

As shown in FIG. 4, the winding-side support shaft 42 is rotated by a winding motor 401 and a driving force transmission 402. The driving force transmission 402 has a torque limiter 403, which shuts off transmission of the driving force to idle the winding motor 401 if the winding-side support shaft 42 comes under an excessive amount of load beyond a predetermined level. Such a load occurs when the ink ribbon R pressed by the printing head 4e is dragged by a running of the medicine packaging sheet S, which leads the ink ribbon R to try to run at the same speed as of the running speed of the medicine packaging sheet S (traveling speed $V_2$). The winding-side support shaft 42 further has a disc section 404a of a rotary encoder (rotation detection section) 404 for detecting a rotating state of the winding-side support shaft 42. The rotating state of the disc section 404a is detected by an optical sensor which is disposed on a circuit board 404b of the rotary encoder 404. The rotary encoder 404 detects the rotation of the winding-side support shaft 42.

The supply-side support shaft 41 also has a disc section 411 of a rotary encoder 410 for detecting a rotating state of the supply-side support shaft 41. The rotating state of the disc section 411 is detected by an optical sensor which is disposed on a circuit board 412 of the rotary encoder 410. The rotary encoder 410 detects the rotation of the supply-side support shaft 41. Further, the supply-side support shaft 41 has a clutch 41a provided by an electromagnetic clutch for example, so that the supply-side support shaft 41 can be switched between a free rotating state and a braking state. The supply-side support shaft 41 is normally kept in the braking state when printing is not performed. The back-up roller 4b has a rotary encoder 4f for detecting its rotating state.

Figure 5:
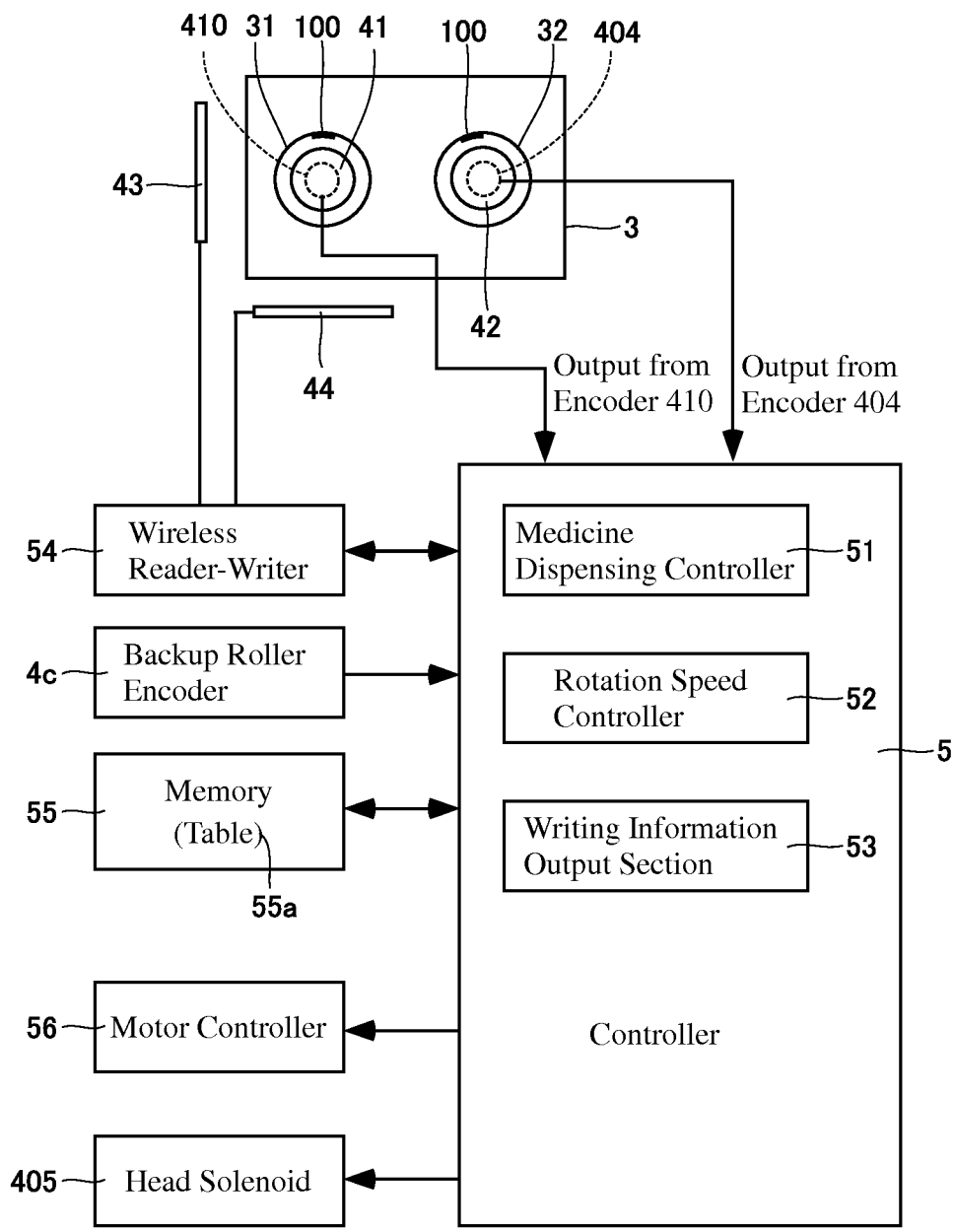
FIG. 5 is a block diagram which shows a control system for ink ribbon operation in the medicine packaging apparatus shown in FIG. 1.

FIG. 5 is a block diagram showing a positional relationship between the antennas 43, 44 and the supply core 31, together with a control system for the medicine packaging apparatus 1. The antennas 43, 44 are connected to a wireless reader-writer 54. The wireless reader-writer 54, which is controlled by a controller 5, reads information from an IC tag (e.g., RFID: Radio Frequency Identification) 100 disposed in the supply core 31 inside the ink ribbon cassette 3, and also writes information to the IC tag 100.

The controller 5 is provided by a microcomputer, functions as a medicine dispensing controller 51 which controls the medicine dispenser unit 11, and also functions as a rotation speed controller 52 for the winding-side support shaft 42 and a writing information output section 53.

The rotation speed controller 52 controls the winding motor 401 which rotates the winding core 32 (the winding-side support shaft 42) of the ink ribbon cassette 3 so that a traveling speed $V_1$ of the ink ribbon R in the winding direction will be greater than a traveling speed $V_2$ of the medicine packaging sheet S, i.e., $V_1 > V_2$, based on a used length of the ink ribbon R that is a piece of information read from the IC tag 100. In the present embodiment, the speed $V_1$ is set to 115% of the speed $V_2$; however, a different value other than 115% may be used. In the ink ribbon cassette 3, there is a constant relationship between the used length of the ink ribbon R, the diameter of the remaining roll of the ink ribbon R which is remaining on the supply core 31, and the diameter of the would roll of the ink ribbon R which is already wound around the winding core 32.

Based on this constant relationship, the rotation speed of the winding-side support shaft 42 can be changed as the used length of the ink ribbon R changes. In this way, it is possible to rotate the winding motor 401 at a speed that moves the ink ribbon R at the speed $V_1$. Also, the torque limiter 403 makes it possible to let the ink ribbon R run at the traveling speed $V_2$ of the medicine packaging sheet S while giving the ink ribbon R a certain amount of tension when the head solenoid 405 is turned ON (under a state where the printing head 4e presses the ink ribbon R).

The torque limiter 403 is set to ON/OFF threshold values which are selected to satisfy the following conditions: more specifically, under the printing state where the ink ribbon R is pulled by the medicine packaging sheet S and is traveling at the speed $V_2$, the ink ribbon R is allowed to travel at the speed $V_2$ even if the ink ribbon R is pulled at the speed $V_1$. Once the printing is finished and the head solenoid 405 is turned OFF so that the ink ribbon R is no longer pulled by or running together with the medicine packaging sheet S, the ink ribbon R is wound at the speed $V_1$. Once the printing is finished, the winding motor 401 is stopped.

During the medicine packaging process, the ink ribbon R is consumed. This used length is added to an original used length at the start of the medicine packaging process, to obtain a total used length, and based on this total, the above-mentioned rotation speed is re-calculated. Also, the used length of the ink ribbon R during the medicine packaging process can be calculated from a winding speed and winding time of the ink ribbon R. It should be noted that in a new ink ribbon roll 30, the IC tag 100 stores information which indicates that the used length is zero.

The IC tag 100 can also be used to store such pieces of information indicating a kind (color, monochrome, etc.) of the ink ribbon R, an outer diameter or a radius of the core (assuming that the supply core 31 and the winding core 32 have the same outer diameter and the radius), a thickness of the ink ribbon R, etc. These pieces of information allow for operating the apparatus accordingly in a case where the core having a different outer radius and/or an ink ribbon R having a different thickness are utilized. A winding roll size (assume it is a radius) as the ink ribbon R is being wound around the winding core 32 can be obtained by adding a thickness of a laminated layer of the ink ribbon (thickness of ink ribbon R×number of windings) to a radius of the winding core 32.

It should be noted here that the winding core 32 is not provided with the antennas 43, 44, or it is not possible to read the outer diameter or the radius of the winding core 32 from the IC tag 100; therefore, when calculating the winding roll size from the core outer diameter or radius, an outer diameter or a radius of the supply core 31 stored in the IC tag 100 is utilized.

The apparatus may include a memory 55 to store a data table 55a containing information about the rotation speed with respect to the used length of the ink ribbon R. In this case, the rotation speed controller 52 provides the data table 55a with information indicating a used length of the ink ribbon R as a read-out address, and obtains rotation speed information which is outputted from the data table 55a. As the ink ribbon R is consumed during the medicine packaging process, this used length is added to the original used length at the start of the medicine packaging process to obtain the total used length, and the obtained total used length is sequentially given to the data table 55a as the read-out address to obtain new rotation speed information. The data table 55a may be provided for each kind of the ink ribbon roll 30, with an arrangement that the kind of the ink ribbon roll 30 attached to the medicine packaging apparatus is read from the IC tag 100.

Under the control provided by the rotation speed controller 52, a motor controller 56 controls driving of the winding motor 401. More specifically, the rotation of winding motor 401 is controlled so that the winding-side support shaft 42 will rotate at a rotation speed w.

The writing information output section 53 outputs information about the total used length of the ink ribbon resulting from the use of the ink ribbon R, to the wireless reader-writer 54. The wireless reader-writer 54 writes this information to the IC tag 100. For example, the rotation speed controller 52 gives sequentially the writing information output section 53 the total used length which is obtained by adding the used length of the ink ribbon R consumed in the medicine packaging process to the original used length at the start of the medicine packaging process. Then, the writing information output section 53 supplies this total used length to the wireless reader-writer 54. The wireless reader-writer 54 sequentially writes the total used length to the IC tag 100.

From the next time, the medicine packaging apparatus 1 may perform a printing operation based on the used length of the ink ribbon R obtained from the IC tag 100.

Figure 6:
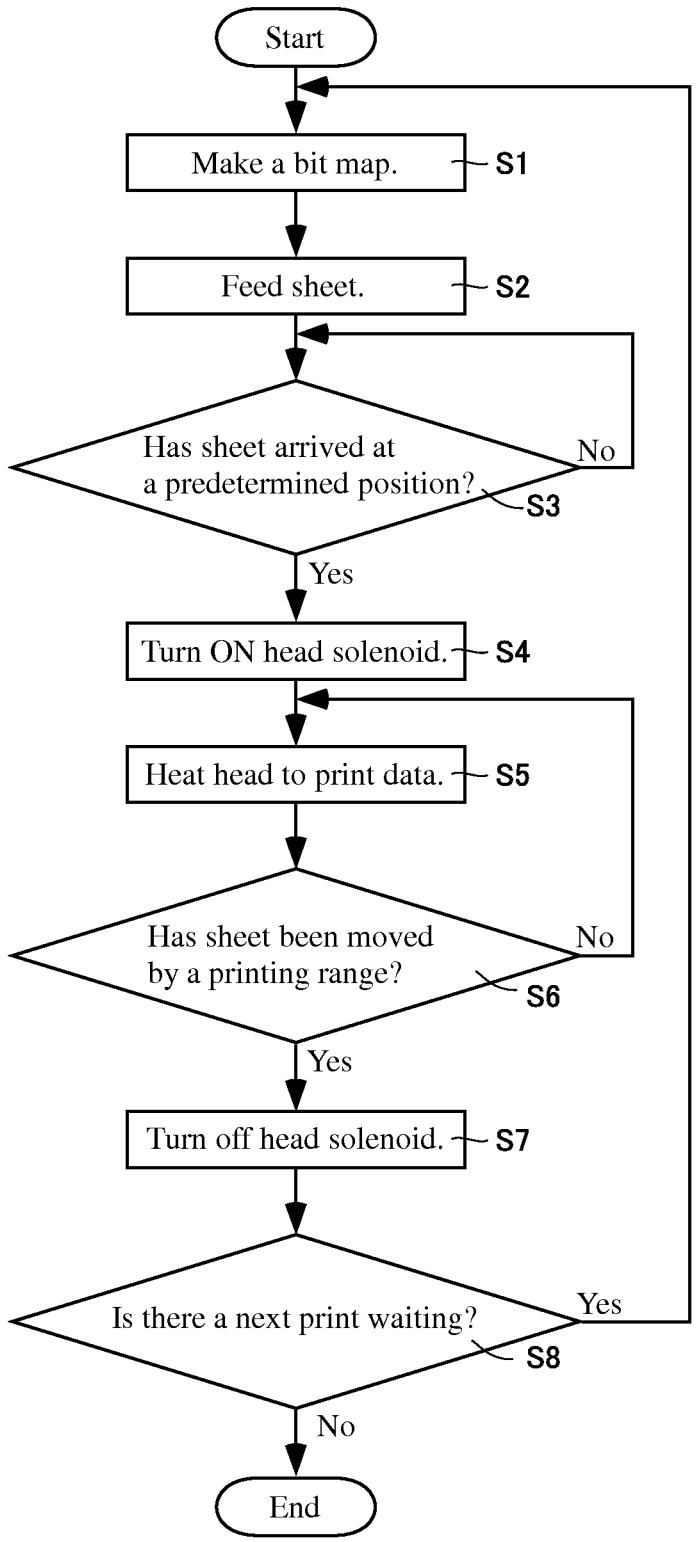
FIG. 6 is a flowchart which shows an overview of a printing process.

Referring next to FIG. 6, a flowchart illustrating an overview of the printing process performed by the controller 5 is shown. The controller 5 performs a bitmapping process from an image which shows the name of the patient, timing of administration, etc. (Step S1). Then, the controller 5 starts a process for making the heater rollers 45d, 45e to thermally seal the packages individually while moving the medicine packaging sheet S (Step S2), and simultaneously therewith, determines if the packaging sheet has arrived at a predetermined location, i.e., if a front edge of an area in the medicine packaging sheet S to be used for the printing is at the location of the printing head 4e, from an operation of the heater rollers 45d, 45e for example (Step S3). Upon determination that the medicine packaging sheet S is at the starting point, the head solenoid 405 is turned ON (Step S4). As the head solenoid 405 is turned ON, the printing head 4e presses the ink ribbon R onto the packaging sheet, causing the ink ribbon R to travel at the speed $V_2$.

In the next step, the controller 5 sends printing data, obtained through the bitmapping process, to the printing head 4e and thermally operates the printing head 4e (Step S5). Then, the controller 5 determines whether the medicine packaging sheet S has been moved to the end of the printing area (Step S6); and if not, brings the process to Step S5; on the other hand, if it is determined that the sheet has been moved completely, then the head solenoid 405 is turned OFF (Step S7). The controller 5 then brings back the process to Step S1 where the printing cycle has to be continued.

Figure 7:
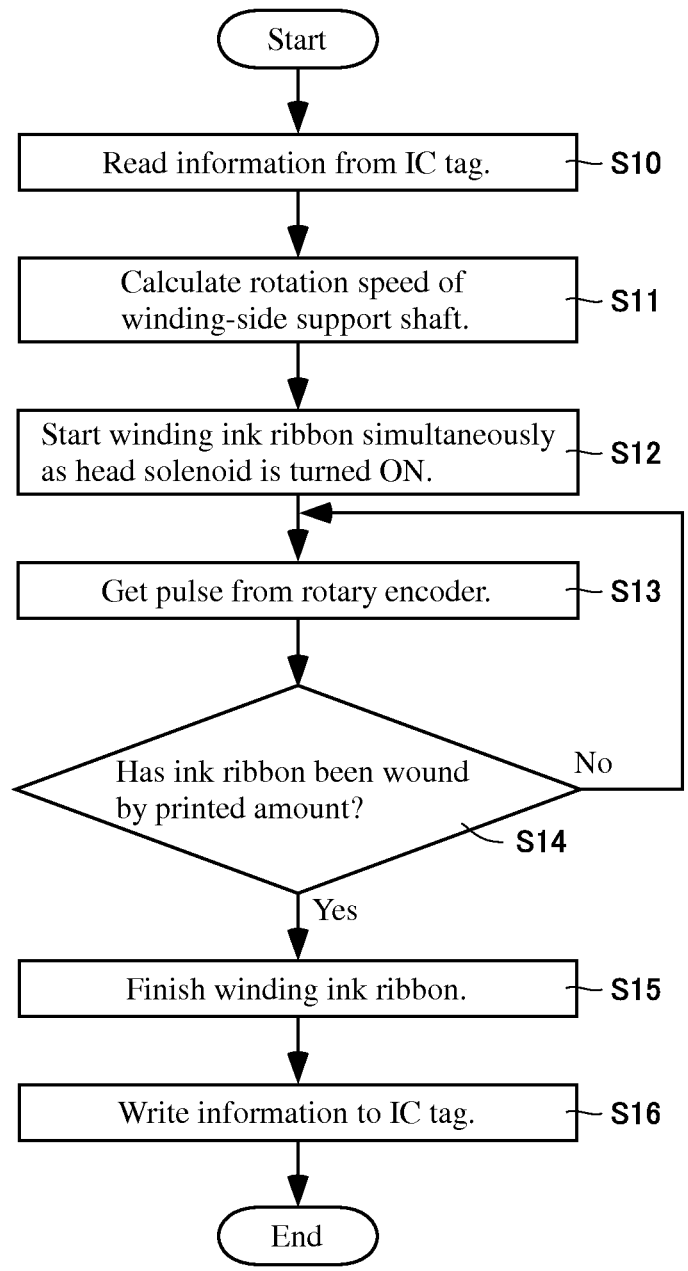
FIG. 7 is a flowchart which shows an overview of an ink ribbon operation.

With reference to FIG. 7, a flowchart illustrating an overview of a travel control on the ink ribbon R performed during the above-described printing process is shown. The controller 5 reads the IC tag 100 and obtains information representing the used length of the ink ribbon R (Step S10), and based on this information, calculates a rotation speed for the winding-side support shaft 42 to achieve the speed $V_1$ (Step S11). Then, right upon the time when the head solenoid 405 is turned ON in the printing cycle shown in FIG. 6, the controller 5 rotates the winding-side support shaft 42 at the rotation speed co which was obtained in the calculation above, to wind the ink ribbon R (Step S12).

In the next step, the controller 5 counts output pulses from the rotary encoder 4f disposed in the back-up roller 4b (Step S13), to determine if the ink ribbon R has been wound by the predetermined amount of printing area (Step S14). If the answer in Step S14 is NO, the above-described determination cycle is continued, whereas if the answer is YES, the winding motor 401 is turned OFF to stop driving of the winding-side support shaft 42, whereby the winding step of the ink ribbon R is brought to an end (Step S15). Thereafter, the controller 5 calculates a new used length based on the newly wound length of the ink ribbon R, and writes this value to the IC tag 100 (Step S16).

As described further above, the information indicating a used length of the ink ribbon R is read from the IC tag 100 which is provided in the supply core 31 of the ink ribbon roll 30 mounted detachably from the ink ribbon cassette 3. Then, based on this information, the winding motor 401 is controlled so that the winding-side support shaft 42 is provided with the rotation speed co which is the speed necessary for obtaining the speed $V_1$ that is faster than the traveling speed $V_2$. This makes it possible to wind the ink ribbon R without slack, without the need for a tension bar. Therefore, there is no longer a need for disposing the tension bar in the medicine packaging apparatus 1, and there is no longer a need for a task of routing the ink ribbon R on the tension bar. Also, the arrangement makes it possible to wind the ink ribbon R at a constant speed rather than in an intermittent manner. This improves printing quality. Although the winding motor 401 is controlled so as to generate the rotation speed w in the winding-side support shaft 42, the torque limiter 403 protects the ink ribbon R from coming under an excessive tension during the printing step while allowing the ink ribbon R to run at the traveling speed $V_2$ of the medicine packaging sheet S.

Figure 8:
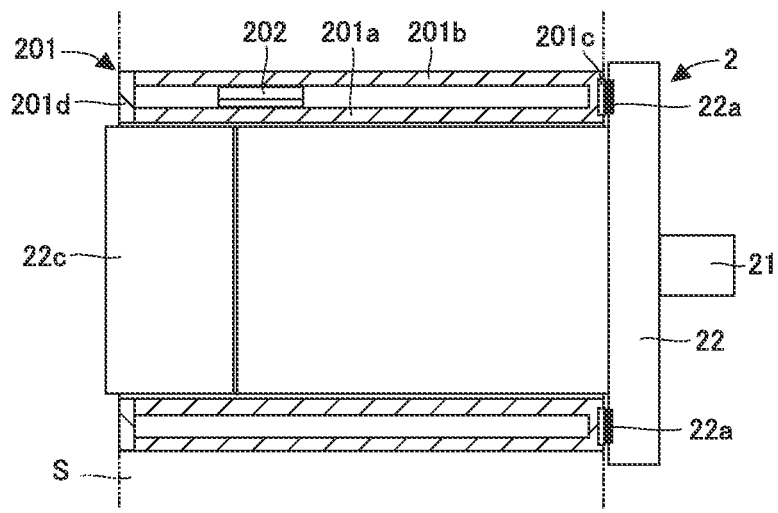
FIG. 8 is a sectional view which shows a core tube and a roll support section of a medicine packaging sheet roll according to one embodiment of the present invention.
Figure 9A:
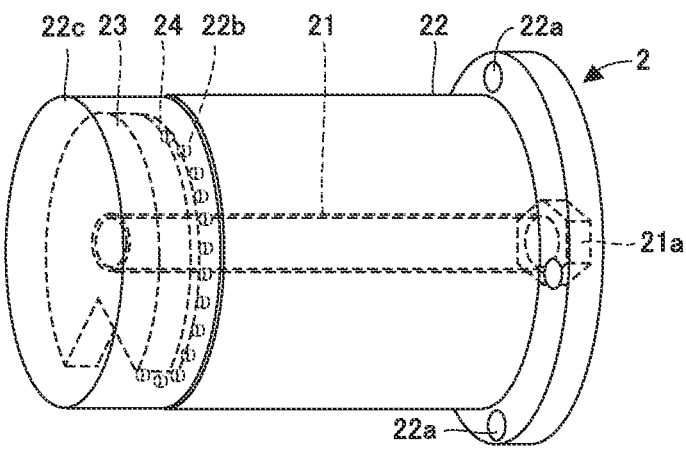
FIG. 9A illustrates a perspective view of a roll support section.
Figure 9B:
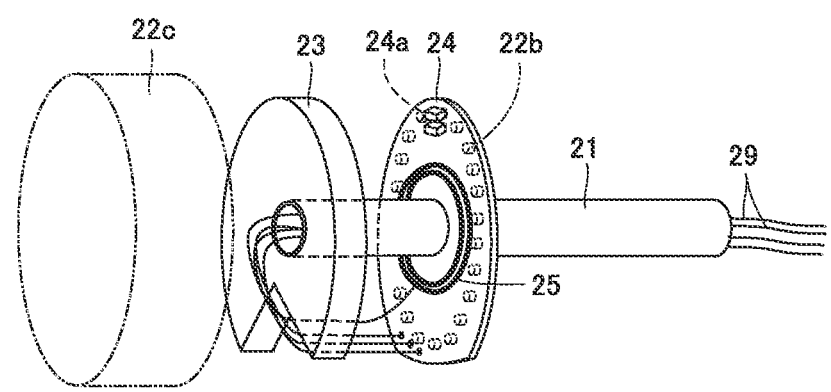
FIG. 9B illustrates a perspective view showing an internal structure of the roll support section.

FIG. 8 is a sectional view of a core tube 201 of the medicine packaging sheet roll 200 mounted on a roll support section 2. FIG. 9A and FIG. 9B are perspective views showing an internal structure of the roll support section 2.

The core tube 201 is constituted by an inner tube portion 201*a* and an outer tube portion 201*b*. The inner tube portion 201*a* and the outer tube portion 201*b* have a gap between them, where there is disposed a storage medium, i.e., a core tube IC tag (provided by, e.g., a RFID: Radio Frequency Identification) 202. At a deep end of the core tube 201, there is provided a ring-shaped, strong magnetic member (iron piece) 201*c*, and at a front end portion of the core tube 201, a ring-shaped lid 201*d* closes the gap.

The roll support section 2 includes a fixed shaft portion 21 and a rotating shaft portion 22 which rotates around the fixed shaft portion 21. The fixed shaft portion 21 has its base-end side provided with a nut 21*a* threaded and tightened, whereby the roll support section 2 is secured to the medicine packaging apparatus 1. When setting the medicine packaging sheet roll 200 to the medicine packaging apparatus 1, the core tube 201 is fitted into the rotating shaft portion 22. The rotating shaft portion 22 has a flange which has its surface provided with, e.g., four magnets 22*a*' that are spaced equidistantly. Once the medicine packaging sheet roll 200 is mounted onto the roll support section 2, the magnets 22*a*' attract the strong magnetic member 201*c*, thereby fixing the core tube 201, and as the medicine packaging sheet roll 200 rotates, the rotating shaft portion 22 rotates.

The rotating shaft portion 22 has a gear section on its base end side. The gear section is engaged with a small gear of a motor which is provided for braking the rotating shaft portion 22. The motor is an AC motor which generates an appropriate braking force when an appropriate DC voltage is provided. According to this sheet tension adjustment of the medicine packaging sheet roll 200 by way of braking, it is possible, as disclosed in JP-B 12 909450 Gazette, to use a sensor which is made of a magnet and a hole element to obtain a remaining diameter of the medicine packaging sheet roll 200, and provide step-wise adjustment of the DC voltage in accordance with the remaining diameter.

The fixed shaft portion 21 has a hollow structure, so it is possible to lay wires 29 therein. On a tip-end side of the fixed shaft portion 21, a circuit board support member 23 is fixed. The circuit board support member 23 supports a circuit board 24. The circuit board 24 is provided, on its one side (on the back-surface side of the circuit board 24 in FIG. 9B), a photo sensor 24*a*, for example, which has a light emitting section and a light receiving section. On the other hand, the circuit board 24 is faced by an end surface of the rotating shaft portion 22, where there is formed twenty-four projections 22*b* (shown by an alternate long and two short dashes lines in FIG. 9B) in a circular pattern, so that as the rotating shaft portion 22 rotates, the projections 22*b* sequentially pass through between the light emitting section and the light receiving section in the photo sensor 24*a*. Thus, a rotation state of the rotating shaft portion 22 is detected by the photo sensor 24*a*. The controller 5 detects an output from the photo sensor 24*a* via the wires 29 and generates a count value, and thus it is possible to know the rotation state of the rotating shaft portion 22. The photo sensor 24*a* outputs the count value as rotation amount information which indicates an amount of rotation of the rotating shaft portion 22; however, the output is not limited to such a count value.

On the other surface of the circuit board 24, an antenna 25 is provided in a spiral shape across an axial direction of the rotating shaft portion 22 (an axial direction of the fixed shaft portion 21). The antenna 25 is also connected to the wires 29. The circuit board support member 23 and the circuit board 24 are covered by a cap 22*c* which is provided on a tip side of the rotating shaft portion 22. Desirably, the core tube IC tag 202 is disposed in such a fashion that its antenna surface does not make a cross with an extension surface along a surface on which the antenna 25 is formed.

Figure 10:
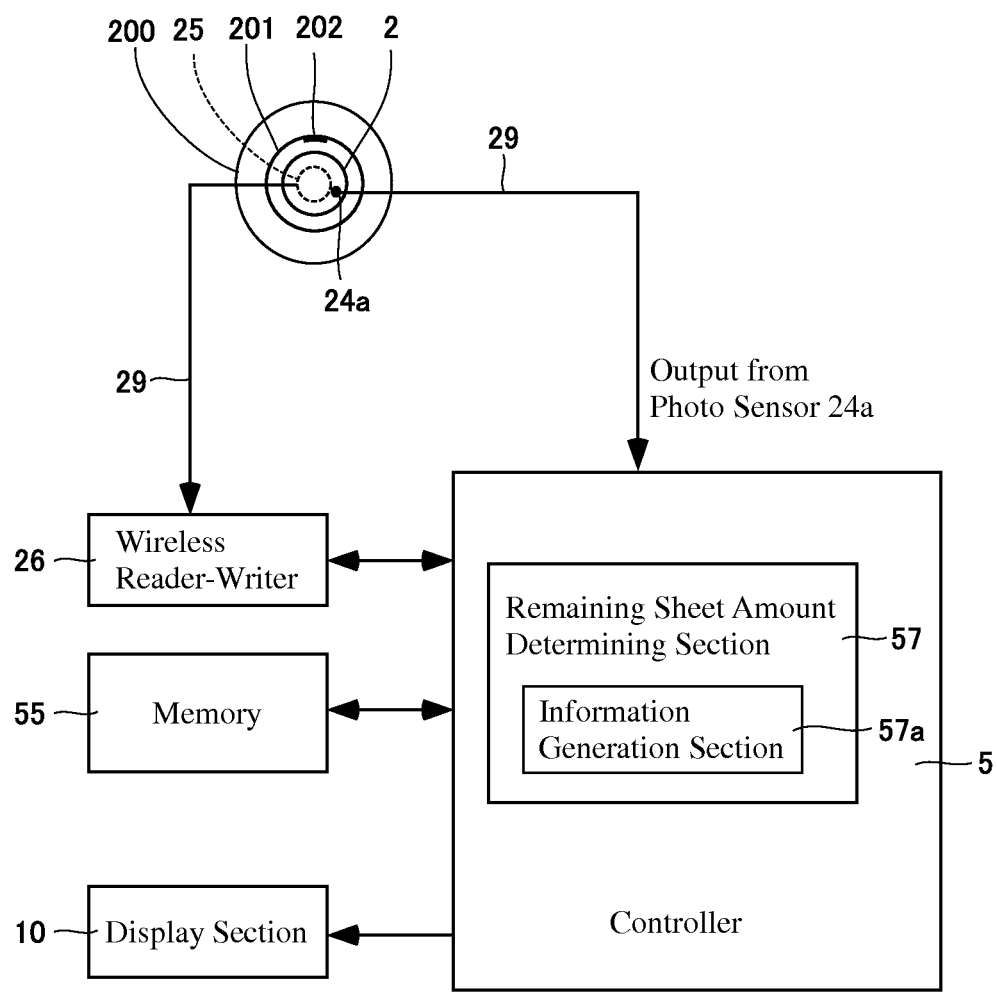
FIG. 10 is a block diagram which shows a control system related to a sheet remaining amount estimation process in the medicine packaging apparatus shown in FIG. 1.

FIG. 10 is an explanatory view illustrating a configuration of the controller 5 as a sheet remaining amount estimation section 57. A wireless reader-writer (information reading section) 26 is controlled by the controller 5, reads information from the core tube IC tag 202 and writes information to the core tube IC tag 202. The information may be encoded or compressed before being written to the IC tag 202 in order to prevent illegal rewriting on the information.

The sheet remaining amount estimation section 57 has an information generation section 57*a*, which generates, as information to be written to the core tube IC tag 202, a count value based on an input from the photo sensor 24*a* upon unwinding of the packaging sheet S from the medicine packaging sheet roll 200 by a predetermined length (e.g., 80 mm as a typical length for one package) at a reference time-point. In the present embodiment, this information represents rotation amount information as of reference sheet-remaining amount timing, and will hereinafter be known as the reference time-point count value (A). The controller 5 can determine whether or not the packaging sheet S has been unwound by the predetermined length, based on, e.g., the amount of rotation of the heater rollers 45*d*, 45*e*.

The information generation section 57*a* also generates a count value based on an output from the photo sensor 24*a* each time the packaging sheet S is unwound from the medicine packaging sheet roll 200 by the predetermined length at a packaging sheet in-use time-point after the reference time-point. In the present embodiment, this information represents a plural pieces of rotation amount information as of a plurality of current sheet-remaining amount timings, and will hereinafter be known as the count value (B) representing a hundred current-time counts. Further, the information generation section 57*a* generates a finished-package count (to be described later as $\alpha_2$), as information indicating an amount of sheet use from the reference time-point to the packaging sheet in-use time-point. The current time-point count values need not necessarily be a plurality of values but may be a single value representing the latest single package at a latest current sheet-remaining amount time-point. The rotation amount information is not limited to the above-mentioned count value. Also, the amount of sheet use from the reference time-point to the packaging sheet in-use time-point is not limited to the finished-package count, but may be represented by a length of the sheet which was consumed, for example.

Figure 12A:
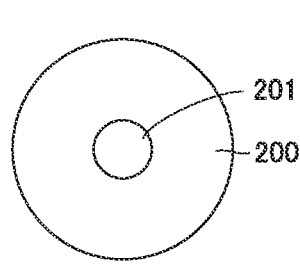
FIGS. 12A-12D represent explanatory views showing a relationship between a packaging sheet used amount at a reference time-point and a packaging sheet used amount at a packaging sheet in-use time-point in the medicine packaging apparatus shown in FIG. 1.
Figure 12B:
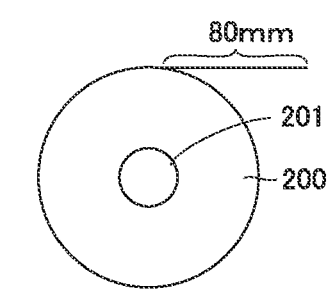
Figure 12C:
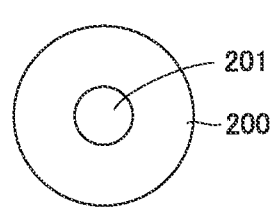
Figure 12D:
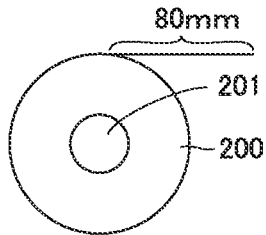

Referring next to FIGS. 12A-12(D), a relationship between a used amount of the packaging sheet at a reference time-point and the used amount of the packaging sheet at a packaging sheet in-use time-point is shown. The reference time-point is a point when the packaging sheet used amount is P. From this state, an amount for one package is unwound by an amount of rotation of the core tube 201 (an amount of rotation from State (A) to State (B) in FIGS. 12A-12B), which represents the amount of rotation at the reference sheet-remaining amount time-point (i.e., the reference time-point count value (A)). The reference time-point count value (A) is used as $x_1$ under a predetermined condition in mathematical expressions which will be described later. Likewise, the packaging sheet in-use time-point is a point when the packaging sheet used amount is Q (Q>P). From this state, an amount for one package is unwound by an amount of rotation of the core tube 201 (an amount of rotation from State (C) to State (D) in FIGS. 12C-12D), This represents the amount of rotation at the current sheet-remaining amount time-point (i.e., the current-time point current value (B)). The current time-point count value (B) is used as $x_2$ under a predetermined condition in mathematical expressions which will be described later. A difference in the packaging sheet used amount between State (A) to State (C) in FIGS. 12A-12C represents the amount of sheet use, and a quotient obtained by a division of the amount of sheet use by a length of a single package is the finished-package count ($\alpha_2$).

The sheet remaining amount estimation section 57 uses the reference time-point count value (A), the current time-point count value (B), the finished-package count ($\alpha_2$) from the reference time-point to the packaging sheet in-use time-point, and dimensional information of the core tube 201 (outer size (diameter, radius), and outer circumference) to estimate a remaining amount of the medicine packaging sheet S which existed at the reference time-point; and from this estimated remaining amount of sheet at the reference time-point, performs a subtracting operation based on the finished-package count, to estimate a current amount of remaining sheet. The controller 5 is capable of using the estimated current amount of remaining sheet to display a quantity of expectable packages in a display section 10.

The controller 5 performs a process if the reference time-point count value is not yet written to the core tube IC tag 202, and performs another process if the value is already written thereto.

In the following, the process of how to estimate the remaining sheet amount of the medicine packaging sheet roll 200 will be described in detail. As information for estimating the remaining sheet amount, the sheet remaining amount estimation section 57 uses the count value (A) as an output from the photo sensor 24a at the reference time-point, and the count value (B) as an output from the photo sensor 24a which is made each time a predetermined amount of sheet unwinding is performed since the reference time-point. Also, for improved accuracy in the estimation of the remaining sheet amount, the count value (B) is obtained each time, and the remaining sheet amount is calculated each time the value is obtained. Then, using an average value of, e.g., a hundred, results of the calculations of the remaining sheet amount, the remaining amount of the packaging sheet S is determined.

[Reference Time-Point Count Value: How to Obtain]

Upon receiving an electric power, the controller 5 reads information from the core tube IC tag 202. If this information reading reveals that there is no reference time-point count value obtained, the process goes to a reference time-point detection preparation step as will be described later in detail with reference to FIG. 11, whereas if there is a reference time-point count value already obtained but no remaining amount calculation information obtained yet, then the process goes further to a packaging sheet remaining amount calculation information collection step, and obtains a reference time-point count value (A).

[Calculation Method]

The remaining amount of sheet as represented by the quantity (y) of packages each made of a 80 mm slip of the sheet; the thickness w (mm) of the sheet; the diameter r (mm) of the core tube 201; and the count value x (times) counted by the photo sensor 24a each time the packaging sheet S is unwound by a predetermined amount, i.e., 80 mm; have an approximate relationship given by Mathematical Expression 1 (MATH 1) shown below: Description will be given later on how to obtain this mathematical expression 1.

$$wy = \frac{3666.9}{x^2} - \frac{(r-w)^2}{320}\pi \quad \text{[MATH 1]}$$

With $y_1$ representing the remaining package quantity (expressed as a quantity of 80 mm sheet slips) at a reference time-point; $x_1$ (an integer) representing a count value obtained by the photo sensor 24a when the packaging sheet S is unwound by the predetermined length, i.e., 80 mm; and $x_2$ (an integer) representing a count value obtained by the photo sensor 24a after the packaging sheet S is unwound for a quantity of $\alpha_2$ packages expressed as a quantity of 80 mm sheet slips each by the predetermined length, i.e., 80 mm, since the reference time-point, the following Mathematical Expression 2 (MATH 2) and Mathematical Expression 3 (MATH 3) are obtained. It should be noted here that in the above, the length for a package and the predetermined length are both 80 mm; however, the length for a package and the predetermined length may be different from the above.

$$y_1 w = \frac{3666.9}{x_1^2} - \frac{(r-w)^2}{320}\pi \quad \text{[MATH 2]}$$

$$(y_1 - \alpha_2)w = \frac{3666.9}{x_2^2} - \frac{(r-w)^2}{320}\pi \quad \text{[MATH 3]}$$

By solving Mathematical Expression 2 and Mathematical Expression 3 for w, the following Mathematical Expression 4 (MATH 4) is obtained:

$$w = \frac{3666.9}{\alpha_2}\left(\frac{1}{x_1^2} - \frac{1}{x_2^2}\right) \quad \text{[MATH 4]}$$

Also, by solving Mathematical Expression 2 and Mathematical Expression 4 for $y_1$, the following Mathematical Expression 5 (MATH 5) is obtained:

$$y_1 = \alpha_2\left(\frac{1}{x_1^2} - 2.6773 \times 10^{-6} \times (r-w)^2\right) \div \left(\frac{1}{x_1^2} - \frac{1}{x_2^2}\right) \quad \text{[MATH 5]}$$

$$= \alpha_2\left(\frac{1}{x_1^2} - 2.6773 \times 10^{-6} \times \left(r - \frac{3666.9}{\alpha_2}\left(\frac{1}{x_1^2} - \frac{1}{x_2^2}\right)\right)^2\right) + \left(\frac{1}{x_1^2} - \frac{1}{x_2^2}\right)$$

Each time the medicine packaging sheet S is unwound by the predetermined amount, i.e., 80 mm, the photo sensor 24a gives a count value, which is then used to substitute the items $x_2$ and $\alpha_2$ in Mathematical Expression 5 to obtain $y_1$. From the ongoing collection of values of $y_1$, an average value of the latest hundred, for example, is utilized to calculate a remaining package quantity as of the reference time-point. Then, from this average value of the hundred $y_1$'s, subtraction is made based on $\alpha_2+1$ packages which is a value obtained by adding one to the finished-package count $\alpha_2$, to obtain an estimated value for a current remaining package quantity (remaining package quantity in State (D) in FIG. 12D). It should be noted here that in case the diameter r (mm) of the core tube 201, which is found in Mathematical Expression 5, is changed at a future time, then the new value is simply put in Mathematical Expression 5. Core tube dimensional information such as the diameter r may be stored in the core tube IC tag 202, or may be stored in the memory 55. The core tube outer diameter may be represented by an inner diameter of the medicine packaging sheet roll 200. In other words, using the inner diameter of the medicine packaging sheet roll 200 is equivalent to using the core tube outer diameter.

[Obtaining Relationship Between Remaining Sheet Amount and Count Value Thereupon]

At a given time point, the medicine packaging sheet roll 200 has a packaging sheet remaining length of Y (mm); the core tube 201 has a circumference of R (mm), and the packaging sheet S has a sheet thickness of w (mm): Then, the remaining length of the packaging sheet S can be interpreted as an addition of circumferences coaxially laminated in n layers, and this is given by Mathematical Expression 6 (MATH 6).

$$Y = R + (R + 2\pi w) + (R + 4\pi w) + \cdots + (R + 2\pi w(n-1)) = \frac{n(R + R + 2\pi w(n-1))}{2} = n(R + (n-1)\pi w) \quad [\text{MATH 6}]$$

By solving the MATH for n, Mathematical Expression 7 (MATH 7) is obtained.

$$n = \frac{\pi w - R + \sqrt{((R - \pi w)^2 + 4\pi w Y)}}{2\pi w} \quad [\text{MATH 7}]$$

As the core tube 201 makes one complete turn, the photo sensor 24a outputs a count value of 24; so when the unwound sheet length is 80 mm, a count value x as the output from the photo sensor 24a is given by Mathematical Expression 8 (MATH 8).

$$x = 24 \times \left( \frac{80}{R + 2\pi n w} \right) \quad [\text{MATH 8}]$$

By placing Mathematical Expression 7 into Mathematical Expression 8, Mathematical Expression 9 (MATH 9) is obtained.

$$x = 24 \times \left( \frac{80}{\pi w + \sqrt{(R - \pi w)^2 + 4\pi w Y}} \right) \quad [\text{MATH 9}]$$

By raising the both sides to the second power and then re-arranging, Mathematical Expression 10 (MATH 10) is obtained. A reason why approximation like in MATH 10 is possible is that the sheet thickness w (mm) of the packaging sheet S is small enough as compared to the circumference R (mm) of the core tube 201 and the packaging sheet remaining length Y (mm) of the sheet tube.

$$\frac{3.6864 \times 10^6}{x^2} = \left( \pi w + \sqrt{(R - \pi w)^2 + 4\pi w Y} \right)^2 \approx (R - \pi w)^2 + 4\pi w Y \quad [\text{MATH 10}]$$

With further rearrangement by using $r=R/\pi$ (core tube diameter [mm]) and $Y=80y$, then Mathematical Expression 11 (MATH 11) is obtained.

$$\frac{3.6864 \times 10^6}{x^2} = (r - w)^2 \pi^2 + 320 \pi w y \quad [\text{MATH 11}]$$

Then, from Mathematical Expression 11, Mathematical Expression 1 is obtained. Although Mathematical Expression 10 obtained as above is an approximate expression, there is no limitation that the expression must be such an approximate expression as described above. Therefore, there is no limitation, either, to Mathematical Expression 1 or any other expressions which are obtained from Mathematical Expression 10. Also, in the above, description was made for a case where the count value given as an output from the photo sensor 24a when the core tube 201 makes one complete turn is 24; the count value given as an output from the photo sensor 24a when sheet unwinding is made by a length of 80 mm is x; and the length of one package is 80 mm. In a case where the count value given as an output from the photo sensor 24a when the core tube 201 makes one complete turn is g; the count value given as an output from the photo sensor 24a when sheet unwinding is made by a length of h mm is x; and the length of one package is j mm, the sheet thickness (w) and the remaining package quantity $y_1$ at the reference time-point are given as follows:

$$w = \frac{(gh)^2}{4\pi \alpha_2 j} \left( \frac{1}{x_1^2} - \frac{1}{x_2^2} \right) \quad [\text{MATH 12}]$$

$$y_1 = \alpha_2 \left( \frac{1}{x_1^2} - \frac{(r-w)^2 \pi^2}{(gh)^2} \right) \div \left( \frac{1}{x_1^2} - \frac{1}{x_2^2} \right) \quad [\text{MATH 13}]$$

Figure 11:
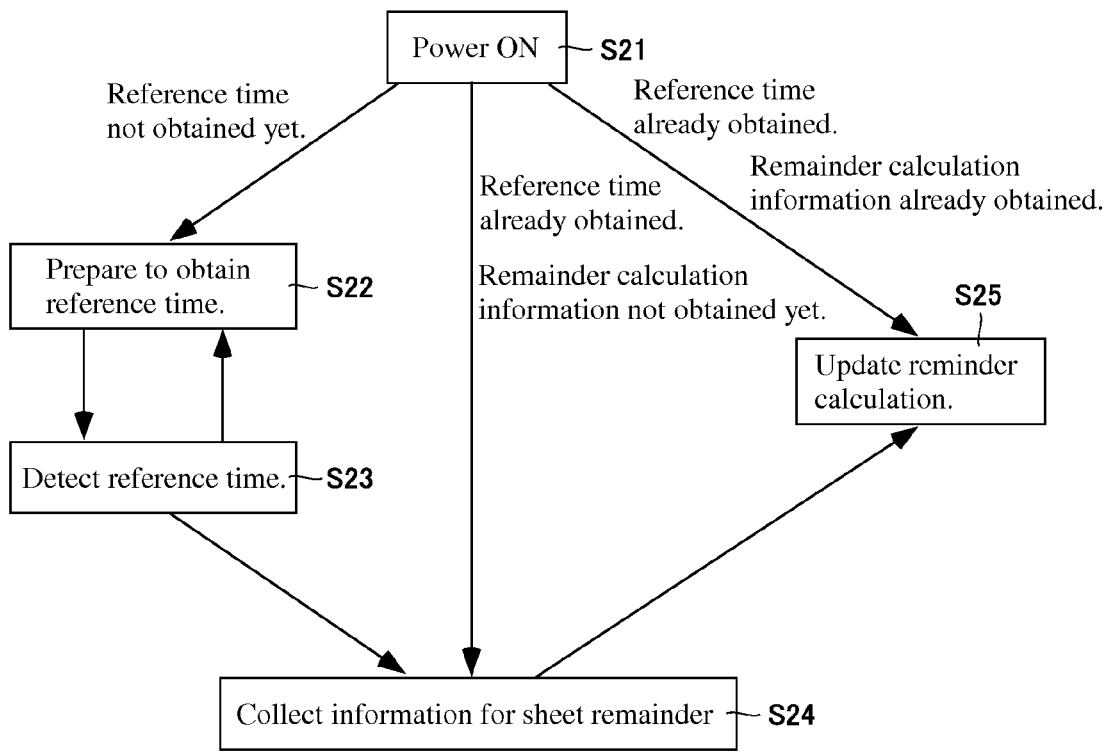
FIG. 11 is an explanatory view which shows a sheet remaining amount estimation process in the medicine packaging apparatus shown in FIG. 1.

Referring next to FIG. 11, an explanatory view illustrating different steps performed by the controller 5 in relation to the packaging sheet remaining amount estimation process is shown.

Upon receiving an electric power (S21), the controller 5 reads information from the core tube IC tag 202. If the obtained information indicates that a reference time-point count value is not yet obtained, then the process goes to a reference time-point detection preparation step (S22); if the information indicates that a reference time-point count value is already obtained but remaining amount calculation information is not, then the process goes to a remaining amount calculation information collection step (S24); and if a reference time-point count value is already obtained and remaining amount calculation information is also already obtained, then the process goes to a remaining amount calculation updating step (S25).

The reference time-point detection preparation step (S22) is a step which is started after the power supply is turned on (S21) or after the process is resumed from a no-more-sheet WARNING. In the reference time-point detection preparation step, each time the packaging sheet S is unwound by a predetermined amount, i.e., 80 mm, a count value as an output from the photo sensor 24a is obtained; and if the latest count value is not different by two or any greater value from the previous value for, e.g., forty times, then it is determined that the apparatus is ready and the process moves to a reference time-point detection step (S23). During the reference time-point detection preparation step, no information for detecting the remaining sheet amount is written to the core tube IC tag 202. Having described as above, the reference time-point detection preparation step (S22) may even be omitted.

In the reference time-point obtaining step (S23), a count value as an output from the photo sensor 24a is obtained each time the packaging sheet S is unwound by 80 mm, for a total of, e.g., nineteen times. An average value (or a mode value) of these is selected to be a count value at, e.g., the tenth cycle, and also to be a count value (A) as an output from the photo sensor 24a at a reference time-point, and then this count value (A) is written to the core tube IC tag 202. The process then moves to the packaging sheet remaining amount calculation information collection step (S24). If, however, the count value as an output from the photo sensor 24a differs by two or by a greater value as compared to the previous value during the above-described nineteen cycles of obtaining a count value, then the reference time-point detection preparation step (S22) is performed again. In the case where the above-described average value is utilized as the tenth count value, the process will use the number "10" as a finished-package count, including one package made in the tenth cycle, from the reference time-point based on the above-described fact that a total of nineteen sheet slips are used.

In the packaging sheet remaining amount calculation information collection step (S24), a count value (B) as an output from the photo sensor 24a is obtained each time the packaging sheet S is unwound by the length of 80 mm. Using this count value (B), a count value (A) at the reference time-point, a finished-package count from the reference time-point, and the diameter r of the core tube 201, a calculation is made to obtain a remaining sheet amount as of the reference time-point. The calculation result is stored in the memory 55. When a set of hundred count values (B) (including the nine values in the above-described case) are obtained, the process moves to the remaining amount calculation updating step (S25). Also, the hundred count values (B) are written to the core tube IC tag 202. Although it is possible to write a remaining length, for example, to the core tube IC tag 202 as an indicator of the remaining sheet amount to be written, the count values (B) are used here due to a capacity limitation of the core tube IC tag 202.

In the remaining amount calculation updating step (S25), a count value (B) as an output from the photo sensor 24a is obtained each time the packaging sheet S is unwound by the length of 80 mm; and a remaining sheet amount as of the reference time-point is calculated. At this stage, the latest one hundred count values (B) are available to calculate a hundred values for the reference time-point remaining sheet amount. Therefore, it is possible to obtain an average value thereof, and then subtract the finished-package count $\alpha_2$ from the obtained average, to get a latest remaining sheet amount calculation result. Each time the remaining sheet amount is calculated, the oldest of the hundred remaining sheet amount calculation results stored in the memory 55 is overwritten by the latest calculation result. Likewise, in the core tube IC tag 202, the oldest count value (B) of the hundred count values (B) is overwritten by the latest count value (B). As described further above with reference to FIGS. 12A-12D, the reference time-point count value (A) is an amount of rotation of the core tube 201 when one package amount is unwound at the reference time-point, from a state where the packaging sheet used amount is P. Therefore, the current amount of remaining sheet can be estimated more accurately if this one-package amount is counted: In other words, the remaining sheet amount calculation result which is given by subtracting the finished-package count $\alpha_2+1$ from the average value is better than the remaining sheet amount calculation result which is given by subtracting the finished-package count $\alpha_2$ from the average value.

As has been described, the remaining amount of the medicine packaging sheet S as of the reference time-point is estimated on the basis of the reference time-point count value, the current time-point count value, the finished-package count which is a count from the reference time-point to the packaging sheet in-use time-point, and the core tube dimensional information. It is not necessary to use the sheet thickness of the medicine packaging sheet S or the thickness of air layers in the calculation of the remaining amount. In other words, it is possible to provide an accurate information on the remaining sheet amount to the user. It may take some time, however, from the time when the reference time-point count value is obtained till the time when the value of remaining sheet amount displayed for the user becomes stable. During this unstable period, the remaining sheet amount to be displayed for the user may be obtained from a different method: For example, the remaining sheet amount may be determined from the diameter of the medicine packaging sheet roll 200 and the sheet thickness of the packaging sheet S.

When a reference time-point count value is not found in information written in the core tube IC tag 202, the controller 5 obtains a count value each time the packaging sheet S is unwound from the medicine packaging sheet roll 200 by a predetermined length (e.g., 80 mm), and repeats this process until a difference between the current and the previous count values is within a predetermined range for a predetermined number of times (e.g., forty times), and thereupon moves the process to a process of obtaining the reference time-point count value. Generally, the medicine packaging sheet roll 200 has a tendency that its outer layers are slackened, the layers of air therebetween do not have a consistent thickness, and the count value tends to vary in a wide range. The reference time-point detection preparation step described above makes it possible to eliminate chances for giving an inaccurate remaining sheet amount calculated from inconsistent values.

Also, the invention prevents inaccurate remaining sheet amount from being calculated, because the controller 5 performs, as a process of obtaining the reference time-point count value, a process of obtaining a count value at a time when the packaging sheet S is unwound from the medicine packaging sheet roll 200 by a predetermined length (e.g., 80 mm) and repeats this process a plurality (e.g., nineteen times) of times; calculate an average value of these values and make the average as a count value for a specific measurement timing (e.g., tenth time); and uses this count value of the specific measurement timing as the reference time-point count value.

Embodiments of the present invention prevents inaccurate remaining sheet amount from being calculated in the following way: the controller 5 performs a process of obtaining a current time-point count value upon unwinding of the packaging sheet S from the medicine packaging sheet roll 200 by a predetermined length (e.g., 80 mm) and writing the obtained value to the core tube IC tag 202, and may repeats this process for a single or a plurality of times if the reference time-point count value is already written in the core tube IC tag 202 but a current time-point count value of a plurality (e.g., 100) of values is not; while obtaining a current time-point count value each time the packaging sheet S in unwound from the medicine packaging sheet roll 200 by a predetermined length and updating the data by overwriting the oldest current time-point count value in the core tube IC tag 202 with the newly obtained value if the reference time-point count value is already written in the core tube IC tag 202 and a current time-point count value of the above-described one or a plurality (e.g., 100) of current time-point count value are also written.

In addition, writing to the core tube IC tag 202 is made in the form of the count value and not in the form of the remaining sheet amount itself. This provides an advantage that the core tube IC tag 202 need not necessarily be provided by one having a large memory capacity even in the case as described earlier where data to be written includes a hundred of data. Further, in a case where the length of one package is changed from 80 mm to 90 mm for example, a change-over can be made quickly because the count values are already stored.

Another advantage is that because the core tube IC tag 202 stores a current time-point count value(s) for the above-described one or a plurality (e.g., 100) of processes, even if the medicine packaging sheet roll 200 is replaced with another during an operation, it is possible to know a remaining package quantity and a roll diameter of the newly loaded medicine packaging sheet roll 200 readily from a current time-point count value if the core tube IC tag 202 of the newly loaded medicine packaging sheet roll 200 stores one or a plurality of current time-point count value(s). Also, in cases where the DC voltage is applied to the motor which generates a braking force to rotation of the medicine packaging sheet roll 200 and adjusted based on the roll diameter of the medicine packaging sheet roll 200, the DC voltage value can be readily determined from the roll diameter of the newly attached medicine packaging sheet roll 200 without any need for actually rotating the roll.

The IC tag 100 of the ink ribbon cassette 3 and the core tube IC tag 202 may be provided by two identical components. However, this poses a potential problem if the ink ribbon cassette 3 is placed near the roll support section 2, that signals from the IC tag 100 will be received by the antenna 25 in the roll support section 2. This problem can be avoided by such an arrangement that each of the IC tags is assigned a UID (Unique Item identification) so that the controller 5 performs an error procedure if it receives a signal accompanied by an UID which is different from the UID of the tag currently communicating with.

The IC tag 100 of the ink ribbon cassette 3 may be provided by a different kind from that of the core tube IC tag 202. In this case, signals from the IC tag 100 are not misidentified even if the ink ribbon cassette 3 is placed near the roll support section 2. Therefore, even if the ink ribbon cassette 3 is placed near the roll support section 2, sheet remaining amount estimation process can be continued without being interrupted by error processes.

There may be an arrangement that the controller 5 compares a required number of medicine packages found in prescription data to an available number of packages estimated from the current amount of remaining sheet, and issues a warning if a comparison result is out of an acceptable range. The acceptable range is set, for example, to satisfy a condition that the estimated number of packages based on the current amount of remaining sheet must be greater than the required number specified the medicine package prescription, by ten or a greater number of packages. The warning may be made by way of character messages displayed in the display section 10, sounds, etc.

The embodiment described thus far discloses a medicine packaging apparatus which includes: a roll support section 2 which has the rotating shaft portion 22 to which a core tube 201 of the medicine packaging sheet roll 200 is attached; a rotation amount information outputting section (such as the photo sensor 24a) which outputs rotation amount information representing an amount of rotation of the rotating shaft portion 22; an information reading section (such as the wireless reader-writer 26) which writes/reads information to/from a storage medium (such as the core tube IC tag 202) provided in the core tube 201 via an antenna 25 provided in the roll support section 2; an information generation section 57a which generates, as information writable to the storage medium, a first rotation amount which is the rotation amount information upon unwinding of a predetermined length of a packaging sheet from the medicine packaging sheet roll 200 which has a first remaining amount of the packaging sheet, a second rotation amount which is the rotation amount information upon unwinding of the predetermined length of the packaging sheet from the medicine packaging sheet roll 200 which has a second remaining amount of the packaging sheet as a smaller amount than the first amount, and the amount of sheet use (such as finished-package count $\alpha 2$) which is a difference between the first amount and the second amount; and a remaining sheet amount calculation section (remaining sheet amount determining section 57) which calculates an amount of remaining sheet after the packaging sheet is unwound by the predetermined length from the medicine packaging sheet roll 200 which had the second remaining amount of packaging sheet, based on the first rotation amount, the second rotation amount, the amount of sheet use and dimensional information of the core tube 201.

In the above embodiment, a time point when the first amount existed is exemplified by the reference time-point; a time point when the second amount existed is exemplified by the packaging sheet in-use time-point; the first rotation amount is exemplified by the reference time-point count value; and the second rotation amount is exemplified by the current time-point count value. The controller 5 performs a process if the first rotation amount is not yet written to the storage medium (such as the core tube IC tag 202), and also performs another process if the first rotation amount has already been written to the medium.

If the first rotation amount is not yet written to the storage medium, the controller 5 performs a process of obtaining rotation amount information upon unwinding of the packaging sheet of the medicine packaging sheet roll 200 by the predetermined length, for a plurality of times; compares the latest rotation amount information to the previous rotation amount information; and moves to a process of obtaining the first rotation amount if the comparison result continued to be within a predetermined range for a predetermined number of times. As the process of obtaining the first rotation amount, the controller 5 performs a process of obtaining rotation amount information upon unwinding of the packaging sheet of the medicine packaging sheet roll 200 by the predetermined length, for a plurality of times; sets an average value or a mode value thereof as rotation amount information as of a predetermined unwinding timing; and performs a process using this rotation amount information as of the predetermined unwinding timing as the first rotation amount. Also, if the first rotation amount is already written to the storage medium but the second rotation amount, which may include one or a plurality of values for use in calculating the remaining sheet amount, is not yet stored therein, the controller 5 performs a process of obtaining the second rotation amount and writing it to the storage medium upon unwinding of the packaging sheet of the medicine packaging sheet roll 200 by the predetermined length, for one or a plurality of times; and if the first rotation amount is already written to the storage medium and the second rotation amount, i.e., which may include one or a plurality of values for use in calculating the remaining sheet amount, is also stored therein, the controller performs a data updating process of obtaining the second rotation amount and overwriting one or the oldest one of the second rotation amounts in the storage medium with the newly obtained amount each time the packaging sheet of the medicine packaging sheet roll 200 is unwound by the predetermined length.

The embodiment described thus far also discloses a medicine packaging sheet remaining amount determination method for a medicine packaging apparatus which packages medicine by one package by using a medicine packaging sheet roll 200. The method includes: a step of obtaining, from a storage medium (such as the core tube IC tag 202) provided in the core tube 201 of the medicine packaging sheet roll 200, a first rotation amount which is a rotation amount of the core tube 201 of the medicine packaging sheet roll 200 upon unwinding of a predetermined length of a packaging sheet from the medicine packaging sheet roll 200 which has a first remaining amount of the packaging sheet, a second rotation amount which is the rotation amount of the core tube 201 upon unwinding of the predetermined length of the packaging sheet from the medicine packaging sheet roll 200 which has a second remaining amount of the packaging sheet as a smaller amount than the first amount, and an amount of sheet use (such as the finished-package count $\alpha_2$) which is a difference between the first amount and the second amount; and a step of calculating a remaining sheet amount which is an amount after the packaging sheet is unwound by the predetermined length from the medicine packaging sheet roll 200 which had the second remaining amount of the packaging sheet, based on the first rotation amount, the second rotation amount, the amount of sheet use and dimensional information of the core tube.

The rotation amount information as of reference sheet-remaining amount timing and the first rotation amount may be obtained by performing, e.g., a medicine packaging simulation using a medicine packaging sheet roll 200 when shipping the medicine packaging sheet roll 200. The obtained values are recorded in the core tube IC tag 202 which is provided in the core tube 201 of the medicine packaging sheet roll 200. In this case, there is no need, in an actual package making process, for generating the rotation amount information as of reference sheet-remaining amount timing and the first rotation amount and recording these in the core tube IC tag 202. In the above, as the core tube 201 makes one complete turn, a count value as an output from the photo sensor 24a becomes "24". However, this is not limiting at all, and the count value for one complete turn may be greater, for example. If a greater number of counts is used for one complete turn, it will become possible to use one specific count value, rather than an average for example, of a plurality of count values, to determine the remaining sheet amount.

Thus far, embodiments of the present invention have been described with reference to the drawings. However, the present invention is not limited to these illustrated embodiments. Any of these embodiments illustrated thus far may be modified or changed in many ways within the scope or within the equivalence of the present invention. Also, it is possible to obtain a sheet thickness of medicine packaging sheet S from MATH 4 and MATH 12 which were described further above.

In the above description and examples, methods for estimating a remaining amount of the medicine packaging sheet S were described. These methods of estimation may also be used to estimate a remaining amount of the ink ribbon.

It should be noted here that the layer of air is thinner on an inner side of the medicine packaging sheet roll 200 than on the outer side thereof; and the same applies also to variation in the layers of air. Hence, as the medicine packaging sheet roll 200 becomes smaller in its diameter, the layer of air becomes almost zero or air layer variation becomes small enough, so the estimated remaining amount of the medicine packaging sheet S calculated by the medicine packaging apparatus 1 becomes increasingly more accurate as the medicine packaging sheet S is becoming increasingly less in its remaining amount. In particular, the estimation of remaining sheet amount becomes most accurate right before the remaining amount of medicine packaging sheet S becomes zero, i.e., when the remaining amount of medicine packaging sheet S is only one rotation-amount of the core tube 201. Thus, at this point, the apparatus can appropriately let the user know an end timing of the medicine packaging sheet S.

However, there may be an arrangement that the medicine packaging apparatus 1 uses the medicine packaging sheet roll 200 until an end-of-sheet sensor 421 (see FIG. 2 and FIG. 3) detects a zero remaining amount of the medicine packaging sheet S regardless of whether or not the sheet remaining amount estimation section 57 estimates a zero amount for the current amount of remaining sheet. The end-of-sheet sensor 421 may be provided by an optical sensor, in which a light from a light emitter to a light receiver is blocked by the medicine packaging sheet S unwound from the medicine packaging sheet roll 200. The end-of-sheet sensor 421 is disposed, for example, near a traveling route of the medicine packaging sheet roll 200, at a place before the printing head 4e as shown in FIG. 2 and FIG. 3. Due to slight dimensional variation within the medicine packaging apparatus 1, and environmental factors such as temperature, humidity, etc., estimation accuracy by the sheet remaining amount estimation section 57 varies. Consequently therefore, the sheet remaining amount estimation section 57 may estimate a current amount of remaining sheet which is smaller or greater than an actual amount. So, there may be an arrangement that a correction step is included in the estimation method for forthcoming estimations of current amount of remaining sheet, based on whether a current amount of remaining sheet estimated by the sheet remaining amount estimation section 57 is greater or smaller than an actual amount of remaining sheet.

One method, for example, of detecting whether a current amount of remaining sheet estimated by the sheet remaining amount estimation section 57 is greater or smaller than an actual amount of remaining sheet is to determine which of the following events occurs earlier, estimation by the sheet remaining amount estimation section 57 of a zero current amount of remaining sheet or detection by the end-of-sheet sensor 421 of a zero remaining amount of the medicine packaging sheet S. As an example, if the current amount of remaining sheet estimated by the sheet remaining amount estimation section 57 is smaller than the actual amount, then thereafter, an estimated amount of remaining sheet on the medicine packaging sheet roll 200 attached to the medicine packaging apparatus 1 is obtained by using a corrected current amount of remaining sheet which is greater than the originally estimated remaining sheet amount by a predetermined amount. On the other hand, if the current amount of remaining sheet estimated by the sheet remaining amount estimation section 57 is greater than the actual amount, then thereafter, the estimated amount of remaining sheet on the medicine packaging sheet roll 200 attached to the medicine packaging apparatus 1 is obtained by using a corrected current amount of remaining sheet which is smaller than the originally estimated remaining sheet amount by a predetermined amount. The predetermined amount may be set as a length representing one or two packages, for example.

As another variation, there may be an arrangement that after an estimation of zero current remaining amount by the sheet remaining amount estimation section 57 or after a detection of zero current remaining amount by the end-of-sheet sensor 421, the medicine packaging apparatus 1 writes information regarding the medicine packaging apparatus 1 (e.g., information regarding the latest error) to an area in the core tube IC tag 202 which was used for writing count values detected by the photo sensor 24a. Writing such information and then collecting the core tube after the packaging sheet S is finished provides a way to learn operating conditions of the medicine packaging apparatus 1, making it possible to provide appropriate maintenance and improvement to the medicine packaging apparatus 1. The arrangement that information regarding the medicine packaging apparatus 1 is written to the area in the core tube IC tag 202 which was used to record count values detected by the photo sensor 24a provides an additional advantage that an IC tag which has a small storage capacity can be used as the core tube IC tag 202.

In the present embodiment, the printing and packaging unit 4 has a head shifting motor 408 as shown in FIG. 4. The head shifting motor 408 has its rotation shaft provided with an eccentric cam 408a, and the eccentric cam 408a makes contact with a linkage member 406. Also, there is provided a coil spring 409 which pulls the linkage member 406 to be away from the back-up roller 4b. As the eccentric cam 408a rotates, the linkage member 406 moves around the shaft 407 against the urge from the coil spring 409. This movement can make two states: a first state in which the printing head 4e and the back-up roller 4b are separated from each other by an approximate distance of 10 mm for example, and a second state in which the distance is longer, being about 30 mm.

When a distance changing operation as described above is performed and the linkage member 406 is moved thereby, the head solenoid 405, which is connected to the linkage member 406, is also moved with its actuator plunger also moved. When the head solenoid 405 is turned ON in the first state, the actuator plunger of the head solenoid 405 presses the linkage member 406 so the printing head 4e moves toward the back-up roller 4b, to press the ink ribbon R onto the medicine packaging sheet S, so that the apparatus is ready for printing.

The second state makes it easy to replace the ink ribbon cassette 3 and the medicine packaging sheet roll 200. Under the second state, however, the printing head 4e does not press the ink ribbon R of the ink ribbon cassette 3. This can often slacken the ink ribbon R, causing it to electrostatically stick onto the medicine packaging sheet S. This makes it difficult to replace the medicine packaging sheet roll 200, and during the replacement, the ink ribbon R can catch the medicine packaging sheet S of the medicine packaging sheet roll 200. If this happens, the ink ribbon R is wastefully pulled out.

In order to solve this problem, under the second state, the winding motor 401 is turned to rotate the winding core 32 of the ink ribbon cassette 3 thereby winding the slackened portion of the ink ribbon R to eliminate slack in the ink ribbon R. Although the slackened portion of the ribbon has a generally constant length, the ink ribbon R which is wound around the winding core 32 in the form of a roll changes a diameter of the roll, and therefore an amount of the ink ribbon R which is wound by one complete rotation of the winding core 32 is not constant.

In the present embodiment, when rotationally driving the winding motor 401 to wind the slackened amount (e.g. 3 cm or other predetermined amount), the controller 5 uses a value of the used length of the ink ribbon R which is read from the IC tag 100. In other words, the controller 5 uses the used length of the ink ribbon R to obtain a current winding diameter of the ink ribbon roll 30 at the current time-point; uses this diameter to calculate a necessary rotation angle of the winding motor 401 to wind the slackened portion of the ink ribbon R, and drives the winding motor 401 by this rotation angle.

Additionally, there may be an arrangement that when the printing and packaging unit 4 is pulled out of an apparatus main body, this removal is detected by the detection switch 422 (see FIG. 1), and the apparatus is brought into the second state. In this case, the apparatus moves into the second state automatically, without requiring a switching operation by the operator. The ink ribbon cassette 3 and the medicine packaging sheet roll 200 may be disposed at positions indicated in imaginary lines in FIG. 1. In this case, the printing and packaging unit 4 is drawable, and also is pivotable around a vertical axis, and in such a case as this, an arrangement may be, for example, that shift to the second state is performed if one of the drawing movement and the pivoting movement is detected by, e.g., the detection switch 422.

However, if the apparatus moves into the second state and winds the ink ribbon R every time the detection is made for, e.g., the printing and packaging unit 4 being pulled out, an amount of waste in the ink ribbon R will increase.

To solve this problem, the controller 5 brings the apparatus into the second state and winds the ink ribbon R only upon determination that the ink ribbon roll 30 is already used up to an end of the ink ribbon or the medicine packaging sheet roll 200 is already used up to an end of the sheet at the time when the printing and packaging unit 4 is detected to be pulled out for example. It should be noted here that the ink ribbon R wound around the ink ribbon roll 30 has its rear end portion formed with a light reflecting region for a predetermined length. The controller 5 determines that the ink ribbon R is finished when an unillustrated optical sensor detects the light reflecting region. Also, the controller 5 determines that the packaging sheet S is finished, based on an output from the end-of-sheet sensor 421.

Figure 13:
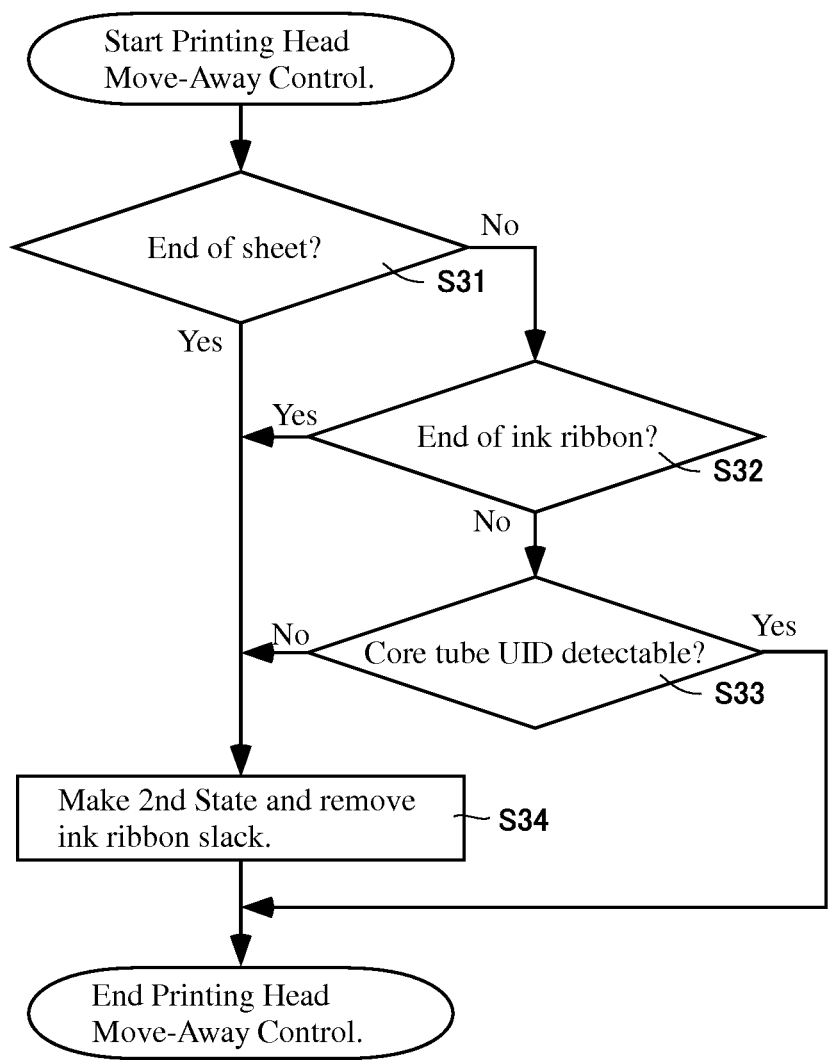
FIG. 13 is a flowchart which shows an example of control performed when the printing and packaging unit shown in FIG. 2 is drawn out of an apparatus main body.

For example, the controller 5 performs a printing head move-away operation if the printing and packaging unit 4 is pulled or pivoted out of the apparatus main body. In the printing head move-away operation, the controller 5 determines, as shown in FIG. 13, whether or not the packaging sheet S is finished (Step S31). If it is determined that the packaging sheet S is finished, then the controller 5 brings the apparatus to the second state and removes a slack in the ink ribbon (Step S34). On the other hand, if it is determined that the packaging sheet S is not yet finished, then a determination is made on whether or not the ink ribbon R is finished (Step S32).

If it is determined that the ink ribbon R is finished, then the controller 5 bring the apparatus into the second state and removes a slack in the ink ribbon (Step S34). In this case, there is very little remainder in the ink ribbon R, so the process may be designed to wind as much of the ink ribbon R as possible. On the other hand, if it is determined that the ink ribbon R is not yet finished, then the controller 5 checks if it is possible to read the UID of the core tube IC tag 202 with the wireless reader-writer 26 (Step S33). If it is impossible to read the UID of the core tube IC tag 202, then the controller brings the apparatus into the second state and removes a slack in the ink ribbon (Step S34). When the medicine packaging sheet roll 200 is being replaced with another, it becomes impossible to read UID of the core tube IC tag 202 because the core tube 201 is removed from the rotating shaft portion 22.

If the UID of the core tube IC tag 202 is obtained, then the printing head move-away operation is brought to an end. It should be noted here that in the present embodiment, the process keeps checking if the UID of the core tube IC tag 202 can be read, until the process detects that the printing and packaging unit 4 is set into the apparatus main body. Upon detection that the printing and packaging unit 4 is returned into the apparatus main body, then the printing head move-away operation is brought to an end.

As described further above, the apparatus is brought into the second state and a slack in the ink ribbon R is removed only when it is determined that there is a possibility that the ink ribbon roll 30 or the medicine packaging sheet roll 200 will be replaced. Therefore, it is possible to drastically reduce waste of the ink ribbon R as compared to an arrangement that a winding operation is performed to remove a slack every time the printing and packaging unit 4 is moved.

The determination made in Step S34 may be replaced by a determination based on an output from a dedicated sensor (such as a sensor for detecting the strong magnetic member 201*c*) which is provided specifically for detection of whether or not the core tube 201 is removed from the rotating shaft portion 22. In other words, there may be an arrangement that the controller 5 determines that there is a possibility for a replacement of the medicine packaging sheet roll 200 when the dedicated sensor has detected that the core tube 201 is removed from the rotating shaft portion 22.

It should be noted here that when removing the slack in the ink ribbon R by winding the ink ribbon R, braking should be applied onto the supply-side support shaft 41 by means of the clutch 41*a*. Also, after the replacement of, e.g., the medicine packaging sheet roll 200, the printing and packaging unit 4 is returned into the apparatus main body by way of pivoting or other movement. This movement should be detected by, e.g., the detection switch 422, so that the controller 5 drives the head shifting motor 408 to change from the second state to the first state.

Upon changing from the second state to the first state, the printing head 4*e* presses the ink ribbon R which is already under a tension since all slack has been removed in the second state. If the clutch 41*a* is still braking on the supply-side support shaft 41 at this time, the ink ribbon R can become unbearable to the tension and be torn.

To avoid this, in the present embodiment, the braking by the clutch 41*a* to the supply-side support shaft 41 is disengaged when changing from the second state to the first state. This prevents the damage to the ink ribbon R reliably.

While the principles of the disclosure have been described above in connection with specific apparatuses, it is to be clearly understood that this description is made only by way of example and not as limitation on the scope of the invention.

The invention claimed is:

1. A medicine packaging apparatus comprising:
   a roll support section including a rotating shaft portion to which a core tube of a medicine packaging sheet roll is attached;
   a rotation amount information outputting section for an output of rotation amount information which indicates a rotation amount of the rotating shaft portion;
   an information reading section for writing information to and reading the written information from a storage medium provided inside the core tube attached to the roll support section;
   an information generation section for generation of, as information writable to the storage medium: rotation amount information as of reference sheet-remaining amount timing which is the rotation amount information upon unwinding of a packaging sheet by a predetermined length from the medicine packaging sheet roll at a reference time-point; one or a plural pieces of rotation amount information as of individual current sheet-remaining amount obtaining timings each of which is the rotation amount information upon unwinding of the packaging sheet by the predetermined length from the medicine packaging sheet roll at a packaging sheet in-use time-point after the reference time-point; and an amount of sheet use from the reference time-point through the packaging sheet in-use time-point; and
   a remaining sheet amount estimation section for estimation of a current amount of remaining sheet based on the rotation amount information as of reference sheet-remaining amount timing, the rotation amount information as of individual current sheet-remaining amount obtaining timing, the amount of sheet use from the reference time-point through the packaging sheet in-use time-point, and dimensional information of the core tube.

2. The medicine packaging apparatus according to claim 1, further comprising a controller for performing of an operation if the rotation amount information as of reference sheet-remaining amount timing is not yet written to the storage medium, and performing of another operation if the rotation amount information as of reference sheet-remaining amount timing is already written thereto.

3. The medicine packaging apparatus according to claim 2, wherein if the rotation amount information as of reference sheet-remaining amount timing is not yet written to the storage medium, the controller performs a process of obtaining rotation amount information for a plurality of times each time the packaging sheet is unwound from the medicine packaging sheet roll by the predetermined length until a latest rotation amount information is within a predetermined range with respect to a previous rotation amount information for a predetermined number of times, whereupon the controller moves to a process of obtaining the rotation amount information as of reference sheet-remaining amount timing.

4. The medicine packaging apparatus according to claim 3, wherein, as the process of obtaining the rotation amount information as of reference sheet-remaining amount timing, the controller performs a process of: obtaining rotation amount information for a plurality of times each time the packaging sheet is unwound from the medicine packaging sheet roll by the predetermined length; calculating an average value or a mode value of information and setting the calculated value as rotation amount information as of a predetermined unwinding timing; and then performs a process using this rotation amount information as the rotation amount information as of reference sheet-remaining amount timing.

5. The medicine packaging apparatus according to claim 2, wherein if the rotation amount information as of reference sheet-remaining amount timing is already written to the storage medium but said one or plural pieces of rotation amount information as of individual current sheet-remaining amount obtaining timings, which are to be used in estimation of the remaining sheet amount, are not yet written, then the controller performs a process of obtaining rotation amount information as of individual current sheet-remaining amount obtaining timing and writing it to the storage medium upon unwinding of the packaging sheet from the medicine packaging sheet roll by the predetermined length, for a single or a plurality of times, whereas if the rotation amount information as of reference sheet-remaining amount timing is already written to the storage medium and said one or plural pieces of rotation amount information as of individual current sheet-remaining amount obtaining timing for use in the estimation are also written, then the controller performs a data updating process of obtaining rotation amount information as of individual current sheet-remaining amount obtaining timing each time the packaging sheet is unwound from the medicine packaging sheet roll by the predetermined length, and using the obtained information to overwrite one or an oldest piece of rotation amount information as of individual current sheet-remaining amount obtaining timing in the storage medium.

6. The medicine packaging apparatus according to claim 1, wherein information sending/receiving between the storage medium and the information reading section is made via antennas disposed in the roll support section, the antennas having their faces disposed in planes extending across an axis of the rotating shaft portion.

7. The medicine packaging apparatus according to claim 1, wherein the apparatus makes comparison between an amount of sheet required to finish a medicine packaging task and the remaining sheet amount, and issues a warning if a comparison result is out of an acceptable range.

8. A medicine packaging sheet roll for use in the medicine packaging apparatus according to claim 1, wherein the roll has the storage medium in the core tube.

9. The medicine packaging sheet roll according to claim 8, for the medicine packaging apparatus, wherein the storage medium stores dimensional information of the core tube.

10. The medicine packaging sheet roll according to claim 8, for the medicine packaging apparatus, wherein the core tube includes an inner tube portion and an outer tube portion, the storage medium being disposed in a gap between the inner tube portion and the outer tube portion.

11. A medicine packaging apparatus comprising:
a roll support section including a rotating shaft portion to which a core tube of a medicine packaging sheet roll is attached;
a rotation amount information outputting section for an output of rotation amount of the rotating shaft portion;
an information generation section for generation of: a first rotation amount upon unwinding of a predetermined length of a packaging sheet from the medicine packaging sheet roll which has a first remaining amount of the packaging sheet; a second rotation amount upon unwinding of the predetermined length of the packaging sheet from the medicine packaging sheet roll which has a second remaining amount of the packaging sheet, the second remaining amount being a smaller amount than the first amount; and an amount of sheet use which is a difference between the first amount and the second amount; a communications section which writes/reads information generated by the information generation section to/from a storage medium provided in the core tube; and
a remaining sheet amount calculation section for calculation of an amount of remaining sheet after the packaging sheet is unwound by the predetermined length from the medicine packaging sheet roll which has the second remaining amount of packaging sheet, based on information read by the communications section and dimensional information of the core tube.

12. The medicine packaging apparatus according to claim 11, further comprising a controller for performing of an operation if the first rotation amount is not yet written to the storage medium, and performing of another operation if the first rotation amount is already written thereto.

13. The medicine packaging apparatus according to claim 12, wherein if the first rotation amount is not yet written to the storage medium, the controller performs a process of obtaining rotation amount information for a plurality of times each time the packaging sheet is unwound from the medicine packaging sheet roll by the predetermined length, until a latest rotation amount is within a predetermined range with respect to a previous rotation amount for a predetermined number of times, whereupon the controller moves to a process of obtaining the first rotation amount.

14. The medicine packaging apparatus according to claim 13, wherein, as the process of obtaining the first rotation amount, the controller performs a process of: obtaining rotation amount for a plurality of times each time the packaging sheet is unwound from the medicine packaging sheet roll by the predetermined length; calculating an average value or a mode value of the rotation amount and setting the calculated value as a rotation amount as of a predetermined unwinding timing; and then performs a process using this rotation amount as the first rotation amount.

15. The medicine packaging apparatus according to claim 12, wherein if the first rotation amount is already written to the storage medium but the second rotation amount, which can include a single or a plurality of values for use in calculation of the remaining sheet amount, is not yet written, then the controller performs a process of obtaining the second rotation amount and writing it to the storage medium upon unwinding of the packaging sheet from the medicine packaging sheet roll by the predetermined length, for a single or a plurality of times, whereas if the first rotation amount is already written to the storage medium and the second rotation amount, which can include a single or a plurality of values for use in the calculation, is also written, then the controller performs a data updating process of obtaining the second rotation amount each time the packaging sheet is unwound from the medicine packaging sheet roll by the predetermined length, and using the obtained amount to overwrite one or an oldest value of the second rotation amount in the storage medium.

16. A medicine packaging apparatus for packaging medicine by one package by using a medicine packaging sheet roll, the apparatus comprising:
a rotation amount information outputting section for an output of rotation amount information as an indication of a rotation amount of a rotating shaft portion to which a core tube of the medicine packaging sheet roll is attached;
a used-amount information outputting section for an output of used-amount information as an indication of an unwound amount of the packaging sheet of the medicine packaging sheet roll;
an information reading section for reading rotation amount information as of reference sheet-remaining amount timing, which is rotation amount information indicating a rotation amount of the core tube of the medicine packaging sheet roll upon unwinding of the medicine packaging sheet roll by a predetermined length at a reference time-point, from a storage medium provided in the core tube of the medicine packaging sheet roll;
an information generation section for generation of: rotation amount information as of individual current sheet-remaining amount obtaining timing which includes one or a plural pieces of rotation amount information indicating a rotation amount of the core tube of the medicine packaging sheet roll each upon unwinding of the medicine packaging sheet roll by the predetermined length at packaging sheet in-use time-points after the reference time-point; and an amount of sheet use from the reference time-point through the packaging sheet in-use time-point; and;
a remaining sheet amount estimation section for estimation of a current amount of remaining sheet based on the rotation amount information as of reference sheet-remaining amount timing, the rotation amount information as of individual current sheet-remaining amount obtaining timing, the amount of sheet use from the reference time-point through the packaging sheet in-use time-point, and dimensional information of the core tube.

17. A medicine packaging sheet remaining amount determination method of a medicine packaging apparatus for packaging medicine by one package by using a medicine packaging sheet roll; the method comprising:
a step of obtaining from a storage medium provided in a core tube of the medicine packaging sheet roll, rotation amount information as of reference sheet-remaining amount timing, which is rotation amount information indicating a rotation amount of the core tube of the medicine packaging sheet roll upon unwinding of the medicine packaging sheet roll by a predetermined length at a reference time-point; rotation amount information as of individual current sheet-remaining amount obtaining timing which includes one or a plural pieces of rotation amount information indicating a rotation amount of the core tube of the medicine packaging sheet roll each upon unwinding of the medicine packaging sheet roll by the predetermined length at a packaging sheet in-use time-point after the reference time-point; and an amount of sheet use from the reference time-point through the packaging sheet in-use time-point; and a step of estimating a current amount of remaining sheet based on the rotation amount information as of reference sheet-remaining amount timing, the rotation amount information as of individual current sheet-remaining amount obtaining timing, the amount of sheet use from the reference time-point through the packaging sheet in-use time-point, and dimensional information of the core tube.

18. A medicine packaging sheet roll for use in the medicine packaging sheet remaining amount determination method according to claim 17, wherein the medicine packaging sheet roll has a storage medium in the core tube.

19. A medicine packaging sheet remaining amount determination method of a medicine packaging apparatus for packaging medicine by one package by using a medicine packaging sheet roll, the method comprising: a step of obtaining, from a storage medium provided in a core tube of the medicine packaging sheet roll, a first rotation amount which is a rotation amount of the core tube of the medicine packaging sheet roll upon unwinding of a predetermined length of a packaging sheet from the medicine packaging sheet roll which has a first remaining amount of the packaging sheet, a second rotation amount which is the rotation amount of the core tube upon unwinding of the predetermined length of the packaging sheet from the medicine packaging sheet roll which has a second remaining amount of the packaging sheet as a smaller amount than the first amount, and an amount of sheet use which is a difference between the first amount and the second amount; and a step of calculating a remaining sheet amount which is an amount after the packaging sheet is unwound by the predetermined length from the medicine packaging sheet roll which had the second remaining amount of packaging sheet, based on the first rotation amount, the second rotation amount, the amount of sheet use and dimensional information of the core tube.

20. A medicine packaging sheet roll for use in the medicine packaging sheet remaining amount determination method according to claim 19, wherein the medicine packaging sheet roll has a storage medium in the core tube.

* * * * *